United States Patent
Watanabe et al.

(10) Patent No.: US 6,825,314 B1
(45) Date of Patent: Nov. 30, 2004

(54) PROCESS FOR THE PREPARATION OF CYCLIC LACTIC ACID OLIGOMERS

(75) Inventors: Mikio Watanabe, Kanagawa (JP); Jiro Takano, Kanagawa (JP); Yoshimi Ishihara, Kanagawa (JP); Masahiro Murakami, Osaka (JP)

(73) Assignee: Amato Pharmaceutical Products, Ltd., Kyoto (JP)

( * ) Notice: Subject to any disclaimer, the term of this patent is extended or adjusted under 35 U.S.C. 154(b) by 0 days.

(21) Appl. No.: 10/070,436

(22) PCT Filed: Sep. 20, 2000

(86) PCT No.: PCT/JP00/06398

§ 371 (c)(1),
(2), (4) Date: Jun. 25, 2002

(87) PCT Pub. No.: WO01/21612

PCT Pub. Date: Mar. 29, 2001

(30) Foreign Application Priority Data

Sep. 20, 1999 (JP) .......................... 11/265715

(51) Int. Cl.$^7$ .............................. C08G 63/00
(52) U.S. Cl. ................. 528/354; 528/355; 528/357; 528/358; 528/359; 525/411; 525/413; 525/415
(58) Field of Search ............... 528/354–355, 528/357–359; 525/411, 413, 415

(56) References Cited

U.S. PATENT DOCUMENTS

| | | | |
|---|---|---|---|
| 5,006,637 A | | 4/1991 | Guggenheim et al. ...... 528/355 |
| 5,043,458 A | * | 8/1991 | Bhatia ..................... 549/274 |
| 5,717,111 A | | 2/1998 | Koehler et al. ............. 549/266 |
| 5,883,222 A | * | 3/1999 | Yanagisawa et al. ........ 528/361 |
| 5,952,455 A | * | 9/1999 | Yanagisawa et al. ........ 528/361 |
| 5,972,879 A | | 10/1999 | Iijima et al. ............... 514/2 |

FOREIGN PATENT DOCUMENTS

| | | |
|---|---|---|
| EP | 0402676 | 12/1990 |
| JP | 3-193731 | 8/1991 |
| JP | 6-306264 | 11/1994 |
| JP | 9-227388 | 9/1997 |
| WO | WO 01/21613 A1 * | 3/2001 |

OTHER PUBLICATIONS

Biochemistry 23(12), pp. 2577–90 (1984).
English Language Abstract of JP 9–227388.
English Language Abstract of JP 6–309264.
Macromolecules 21(2), pp. 286–93 (1988).

* cited by examiner

Primary Examiner—P. Hampton Hightower
(74) Attorney, Agent, or Firm—Greenblum & Bernstein, P.L.C.

(57) ABSTRACT

The object of the present invention is to provide a novel method for effectively producing a cyclic lactic acid oligomer, and a cyclic lactic acid oligomer produced by the method. According to the present invention, there is provided a method for producing a cyclic lactic acid oligomer represented by the following formula (1):

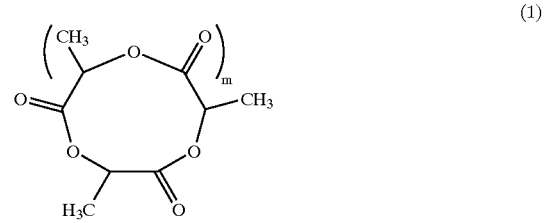

(1)

wherein m represents an integer of 1 to 30, wherein lactides are polymerized in the presence of an alkali metal compound represented by the following formula (2):

$$R—Y—Me \quad (2)$$

wherein R represents an aliphatic group, aromatic group, $—Si(R^{10})(R^{11})(R^{12})$, $—CH(R^{20})CONR^{21}R^{22}$ or $—CH(R^{30})COOR^{31}$, wherein each of $R^{10}$, $R^{11}$ and $R^{12}$ independently represents an aliphatic or aromatic group, $R^{20}$ represents an aliphatic group, each of $R^{21}$ and $R^{22}$ independently represents a hydrogen atom, aliphatic group or aromatic group, $R^{30}$ represents an aliphatic group, and $R^{31}$ represents a hydrogen atom, aliphatic group or aromatic group;

Y represents —O—, —S— or $—NR^{40}—$, wherein $R^{40}$ represents a hydrogen atom, aliphatic group or aromatic group; and Me represents an alkali metal; and, a cyclic lactic acid oligomer produced by the above production method.

20 Claims, 31 Drawing Sheets

PROCESS FOR THE PREPARATION OF CYCLIC LACTIC ACID OLIGOMERS

TECHNICAL FIELD

The present invention relates to a method for producing a cyclic lactic acid oligomer, and a cyclic lactic acid oligomer produced by the production method.

BACKGROUND ART

A lactic acid oligomer having a cyclic structure is a useful compound which is used as a medicament such as a tumor cell growth inhibiting agent (Japanese Patent Application Laying-Open (Kokai) No. 3-193731) or an antineoplastic agent (Japanese Patent Application Laying-Open (Kokai) No. 9-227388), or an intermediate thereof.

The conventional method for producing such a lactic acid oligomer involves subjecting lactic acids to dehydration condensation by heating under an inactive atmosphere, and then separating and collecting an oligomer component from the obtained reaction products.

However, since it is difficult to produce a lactic acid oligomer selectively by this conventional method and that the lactic acid polymer obtained in the dehydration condensation process of lactic acids has a broad molecular weight distribution, containing high polymers, it is necessary to separate and collect a lactic acid oligomer by separation means such as chromatography.

DISCLOSURE OF THE INVENTION

The object of the present invention is to provide a novel method for effectively producing a cyclic lactic acid oligomer, and a cyclic lactic acid oligomer produced by the method.

As a result of concentrated research to achieve the aforementioned object, the present inventors have found that a cyclic lactic acid oligomer can be produced effectively by polymerization of lactides in the presence of a certain alkali metal compound, thereby providing the present invention.

Thus, according to the present invention, there is provided a method for producing a cyclic lactic acid oligomer represented by the following formula (1):

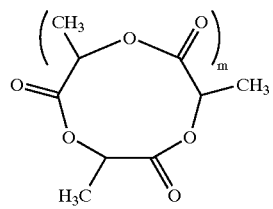

(1)

wherein m represents an integer of 1 to 30,
wherein lactides are polymerized in the presence of an alkali metal compound represented by the following formula (2):

(2)

wherein R represents an aliphatic group, aromatid group, $-Si(R^{10})(R^{11})(R^{12})$, $-CH(R^{20})CONR^{21}R^{22}$ or $-CH(R^{30})COOR^{31}$, wherein each of $R^{10}$, $R^{11}$ and $R^{12}$ independently represents an aliphatic or aromatic group, $R^{20}$ represents an aliphatic group, each of $R^{21}$ and $R^{22}$ independently represents a hydrogen atom, aliphatic group or aromatic group, $R^{30}$ represents an aliphatic group, and $R^{31}$ represents a hydrogen atom, aliphatic group or aromatic group;

Y represents $-O-$, $-S-$ or $-NR^{40}-$, wherein $R^{40}$ represents a hydrogen atom, aliphatic group or aromatic group; and Me represents an alkali metal.

Preferably, the alkali metal compound is a compound of formula (2) wherein R represents an alkyl group having 1 to 12 carbon atoms, aryl group having 6 to 30 carbon atoms, $-Si(R^{10})(R^{11})(R^{12})$, $-CH(R^{20})CONR^{21}R^{22}$ or $-CH(R^{30})COOR^{31}$, wherein each of $R^{10}$, $R^{11}$ and $R^{12}$ independently represents an aliphatic or aromatic group, $R^{20}$ represents an aliphatic group, each of $R^{21}$ and $R^{22}$ independently represents a hydrogen atom, aliphatic group or aromatic group, $R^{30}$ represents an aliphatic group, and $R^{31}$ represents a hydrogen atom, aliphatic group or aromatic group.

Preferably, the alkali metal compound is a compound of formula (2) wherein Y is $-O-$ or $-S-$.

Preferably, the alkali metal compound is a compound of formula (2) wherein Me is lithium.

Preferably, in formula (1), m is an integer of 1 to 21.

According to one embodiment of the present invention, as the alkali metal compound, there is used any of: a compound of formula (2) wherein R is an aliphatic group having 4 or more carbon atoms; a compound of formula (2) wherein R is an aromatic group and Y is $-S-$; or a compound of formula (2) wherein R is $-CH(R^{20})CONR^{21}R^{22}$ wherein $R^{20}$ represents an aliphatic group and each of $R^{21}$ and $R^{22}$ independently represents a hydrogen atom, aliphatic group or aromatic group. In the case of using such alkali metal compounds, cyclic lactic acid oligomer is selectively produced substantially free of chain lactic acid oligomer.

According to another aspect of the present invention, there is provided a cyclic lactic acid oligomer, which is produced by the aforementioned method for producing a cyclic lactic acid oligomer according to the present invention. Preferably, there is provided the cyclic lactic acid oligomer which is substantially free of chain lactic acid oligomer.

THE BEST MODE FOR CARRYING OUT THE INVENTION

Figure 1:
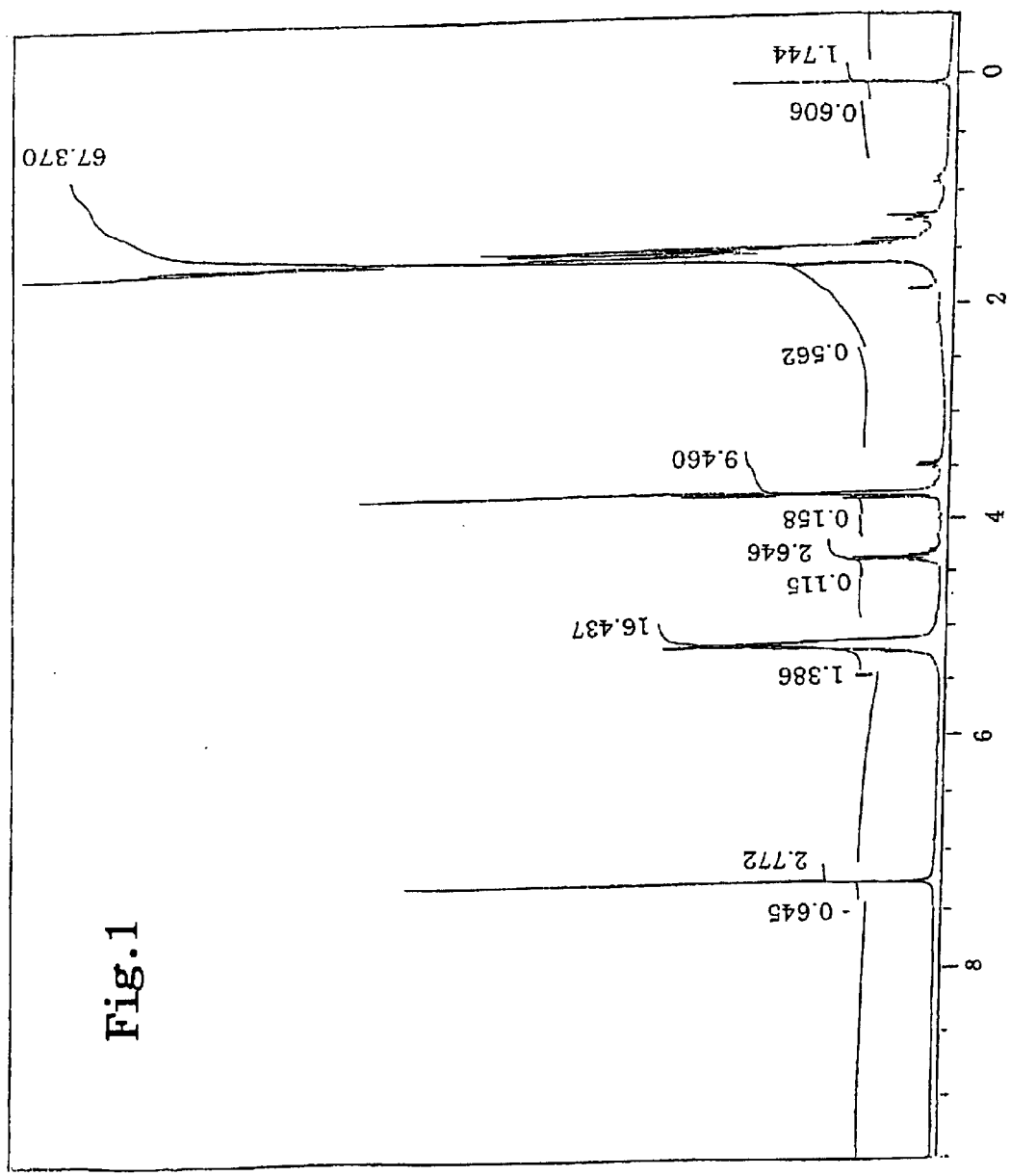
FIG. 1 shows a general view of NMR of the product obtained in Example 1.

The embodiments and methods for carrying out the present invention are described in detail below.

The method for producing a cyclic lactic acid oligomer of the present invention is characterized in that lactides are polymerized in the presence of an alkali metal compound represented by the following formula (2):

$$R\text{—}Y\text{—}Me \tag{2}$$

wherein R represents an aliphatic group, aromatic group, $-Si(R^{10})(R^{11})(R^{12})$, $-CH(R^{20})CONR^{21}R^{22}$ or $-CH(R^{30})COOR^{31}$, wherein each of $R^{10}$, $R^{11}$ and $R^{12}$ independently represents an aliphatic or aromatic group, $R^{20}$ represents an aliphatic group, each of $R^{21}$ and $R^{22}$ independently represents a hydrogen atom, aliphatic group or aromatic group, $R^{30}$ represents an aliphatic group, and $R^{31}$ represents a hydrogen atom, aliphatic group or aromatic group;

Y represents —O—, —S— or $-NR^{40}$—, wherein $R^{40}$ represents a hydrogen atom, aliphatic group or aromatic group; and Me represents an alkali metal.

The raw material in the production method of the present invention is lactide (3,6-dimethyl-1,4-dioxane-2,5-dione) obtained by condensation of two molecules of lactic acid by dehydration, and this lactide is reacted in the presence of the alkali metal compound represented by the above-mentioned formula (2). The formula (2):

$$R\text{—}Y\text{—}Me \tag{2}$$

is described below.

In formula (2), R represents an aliphatic group, aromatic group, $-Si(R^{10})(R^{11})(R^{12})$, $-CH(R^{20})CONR^{21}R^{22}$ or $-CH(R^{30})COOR^{31}$, wherein each of $R^{10}$, $R^{11}$ and $R^{12}$ independently represents an aliphatic or aromatic group, $R^{20}$ represents an aliphatic group, each of $R^{21}$ and $R^{22}$ independently represents a hydrogen atom, aliphatic group or aromatic group, $R^{30}$ represents an aliphatic group, and $R^{31}$ represents a hydrogen atom, aliphatic group or aromatic group.

The aliphatic group in the present specification may be a straight chain, branched chain, cyclic, or combined thereof, and may be saturated or unsaturated aliphatic hydrocarbon group having 1 to 12, preferably 1 to 6 carbon atoms. Examples thereof include alkyl groups such as methyl, ethyl, n-propyl, i-propyl, n-butyl, i-butyl, t-butyl, octyl and dodecyl, and cycloalkyl groups such as cyclopropyl, cyclobutyl, cyclooctyl and cyclododecyl. The aliphatic group may be an unsaturated hydrocarbon group having a double or triple bond.

The aromatic group in the present invention may be an aryl group and an arylalkyl group having 6 to 30, preferably 6 to 20, more preferably 6 to 12, and further more preferably 6 to 10 carbon atoms. Examples of the aryl group include phenyl, tolyl and naphthyl, and examples of the arylalkyl group include benzyl, phenethyl and naphthylmethyl.

The aliphatic group and the aromatic group may have one or more substituent(s). The type of substituents is not particularly limited, and examples include a straight chain, branched chain or cyclic alkyl group, a straight chain, branched chain or cyclic alkenyl group, a straight chain, branched chain or cyclic alkynyl group, an aryl group, an acyloxy group, an alkoxycarbonyloxy group, an aryloxycarbonyloxy group, a carbamoyloxy group, a carbonamide group, a sulfonamide group, a carbamoyl group, a sulfamoyl group, an alkoxy group, an aryloxy group, an aryloxycarbonyl group, an alkoxycarbonyl group, an N-acylsulfamoyl group, an N-sulfamoylcarbamoyl group, an alkylsulfonyl group, an arylsulfonyl group, an alkoxycarbonylamino group, an aryloxycarbonylamino group, an amino group, an ammonio group, a cyano group, a nitro group, a carboxyl group, a hydroxyl group, a sulfo group, a mercapto group, an alkylsulfinyl group, an arylsulfinyl group, an alkylthio group, an arylthio group, an ureide group, a heterocyclic group (e.g. a monocyclic or condensed ring containing at least one or more nitrogen, oxygen or sulfur atom(s) and consisting of 3 to 12 ring forming members), a heterocyclic oxy group, a heterocyclic thio group, an acyl group, a sulfamoylamino group, a silyl group, and a halogen atom. In the above description, the carbon number of alkyl, alkenyl, alkynyl and alkoxy is generally 1 to 12, preferably 1 to 6, and the carbon number of aryl is generally 6 to 20, preferably 6 to 10.

In formula (2), Y represents —O—, —S— or $-NR^{40}$—, wherein $R^{40}$ represents a hydrogen atom, aliphatic group or aromatic group. Preferably, Y is —O— or —S—. Examples of aliphatic or aromatic groups represented by $R^{40}$ are as stated above.

In formula (2), Me represents an alkali metal. Examples of alkali metal include Li, Na or K, and Li is preferable.

Among compounds represented by formula (2), the compounds having asymmetric carbon atoms may be any one of (R) form, (S) form, and (R),(S) form.

A method for obtaining an alkali metal compound represented by formula (2) is not particularly limited, and a person skilled in the art can obtain the compound as appropriate. For example, the alkali metal compound can be obtained by reaction of R—YH with an alkylated alkali metal such as n-butyllithium.

Where lactides are polymerized in the presence of an alkali metal compound represented by formula (2) according to the method of the present invention, the amount of alkali metal compound (R—Y—Me) is preferably 0.1 to 1 mole, more preferably 0.2 to 0.3 mole per mole of lactide.

When the method of the present invention is carried out, the reaction temperature is not particularly limited as long as the reaction progresses, and the reaction temperature is preferably −100° C. to room temperature, more preferably −78° C. to −50° C. It is preferable that the reaction is initiated at a temperature of −78° C. to −50° C. and that the reaction is performed while gradually raising the temperature to room temperature.

Polymerization reaction of lactides in the method of the present invention is preferably carried out in the presence of a reaction solvent. The reaction solvent is not particularly limited as long as it is inactive for the reaction, and examples of preferred solvents include cyclic ether such as tetrahydrofuran, diethylether, and dimethoxyethane. Examples of reaction atmospheres may be inactive gas atmospheres such as nitrogen gas and argon gas. Reaction pressure is not particularly limited, and is preferably normal pressure.

Next, the reaction mechanism of production of a cyclic lactic acid oligomer by the method of the present invention is described, but the following theory is not intended to limit the scope of the present invention. The case of using Li as an alkali metal compound is described herein, but it is considered that the reaction mechanism is similar where other alkali metal compounds such as Na or K are used. In the polymerization reaction of lactides in the method of the present invention, first, a lithium compound and lactide are reacted to generate a chain lactic acid derivative represented by the following formula (4):

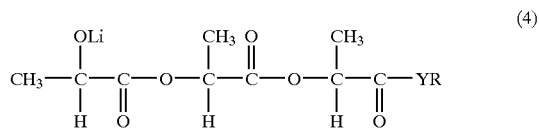

(4)

wherein Y and R are as defined above in the present specification. Then, lactide is reacted with this compound to generate a chain lactic acid oligomer represented by the following formula (5):

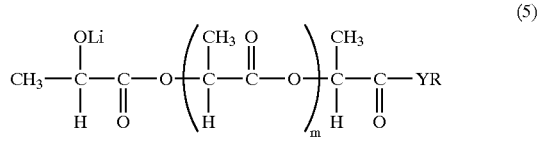

(5)

wherein m, Y and R are as defined above in the present specification. Subsequently, RYLi is removed from this compound, and the compound is cyclized, so that a cyclic lactic acid oligomer of the above formula (1) is considered to be generated.

The composition of a lactic acid oligomer obtained by the method of the present invention is changed depending on an alkali metal compound used as a reaction assistant. For example where the alkali metal compound (preferably a lithium compound) of alkyl alcohol having 1 to 3 carbon atoms is used, a mixture (the ratio of cyclic lactic acid oligomer: 80 to 85% by weight) of a cyclic lactic acid oligomer and a chain oligomer can be obtained. In contrast, where the alkali metal compound of alkyl alcohol having 4 or more carbon atoms such as t-butyl alcohol, or the alkali metal compound of thiophenol and the like, is used, substantially only cyclic lactic acid oligomer can be obtained selectively. Also, substantially only cyclic lactic acid oligomer can be obtained selectively by using, as an alkali metal compound, a compound of formula (2) wherein R is —CH(R$^{20}$)CONR$^{21}$R$^{22}$, wherein R$^{20}$ is an aliphatic group and each of R$^{21}$ and R$^{22}$ is independently a hydrogen atom, aliphatic group or an aromatic group, more specifically, for example, lactic acid amide represented by the following formula (3):

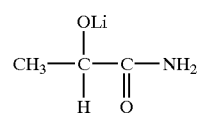

(3)

The term "substantially only cyclic lactic acid oligomer is obtained selectively" is used in the present specification to mean that substantially no chain lactic acid oligomers are generated in a reaction product, and specifically it means that the ratio of chain lactic acid oligomer to total lactic acid oligomer in a reaction product is generally 10% by weight or less, preferably 5% by weight or less, and particularly preferably 3% by weight or less.

As stated above, one advantage of the present invention is that the composition of a cyclic lactic acid oligomer and a chain oligomer in a reaction product can be controlled by selection of the type of an alkali metal compound.

According to the method of the present invention, there is produced a cyclic lactic acid oligomer represented by the following formula (1):

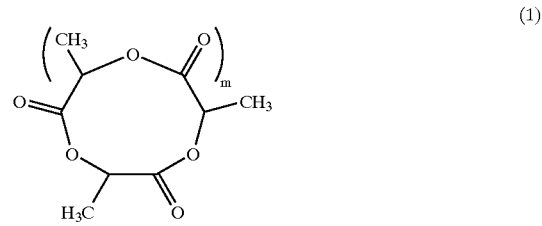

(1)

In formula (1), m represents an integer of 1 to 30, preferably 1 to 21.

The reaction product obtained by the method of the present invention is generally a mixture of cyclic lactic acid oligomers, wherein m represents an integer of 1 to 30, for example, 1 to 28, 1 to 25, 1 to 21, or 1 to 19.

The present invention also relates to a cyclic lactic acid oligomer, which is produced by the aforementioned method for producing a cyclic lactic acid oligomer of the present invention. In a preferred embodiment for the present invention, a mixture of cyclic lactic acid oligomers substantially free of chain lactic acid oligomers can be produced.

The mixture of cyclic lactic acid oligomers produced by the method of the present invention (or a single substance obtained by purification from the mixture) is useful as a tumor cell growth inhibiting agent, an antineoplastic agent, a preventive agent against cancer metastasis, a QOL improving agent for cancer patients, an immune activating agent, and the like, and the mixture can also be used for prevention and/or treatment of diabetes or diabetes complications since it has an action of reducing blood sugar level. Moreover, the mixture of cyclic lactic acid oligomers produced by the method of the present invention (or a single substance obtained by purification from the mixture) has an action of repressing excessive appetite and promoting basal metabolism, and so it can be used also as a medicament useful for improvement and/or prevention of adiposis and enhancement of effects of kinesitherapy, and is also useful as an agent for promoting glycogen accumulation or an agent for enhancing physical fitness. Furthermore, a cyclic lactic acid oligomer produced by the method of the present invention is useful not only as a medicament, but also as health foods or diet supplements including beverages, which is generally called soft drinks, drinkable preparations, health foods, specific hygienic foods, functional foods, function activating foods, nutritional supplementary foods, supplements, feed, feed additives, and the like.

The present invention is further described in the following examples. It is apparent to those skilled in the art that materials, usage, proportion, treatment, treatment process and the like shown in the following examples can be modified as appropriate, as long as the modifications are within the spirit and scope of the invention, and the examples are not intended to limit the scope of the invention.

EXAMPLES

Example 1

A THF solution (2 ml) in which 0.033 g (1.03 mmol) of methanol was dissolved was added to a 50 ml double-cap eggplant-shaped flask under a nitrogen atmosphere, and cooled to −78° C. in a dry ice/acetone bath. Then, 0.64 ml (1.00 mmol) of n-butyllithium was added thereto and the mixture was stirred for 15 minutes. Further, a THF solution (2 ml) in which 0.576 g (4.00 mmol) of (3R,6R)-(+)-3,6-dimethyl-1,4-dioxane-2,5-dione was dissolved was added thereto and stirred, and the temperature was gradually raised to room temperature over 4 hours.

After completion of stirring, 2 ml of saturated ammonium chloride was added to the mixture while maintaining a nitrogen atmosphere, and 10 ml of water was further added thereto. The mixture was extracted with chloroform and a saturated saline solution and washed, and then anhydrous sodium sulfate was added thereto and dried overnight. The obtained product was subjected to vacuum concentration in which solvent was completely removed with a vacuum pump. As a result, 0.551 g (yield 90.5%) of product consisting of a mixture of cyclic oligo-lactate and chain oligo-lactate was obtained with a weight ratio between cyclic oligomer and chain oligomer being 84:16.

Figure 2:
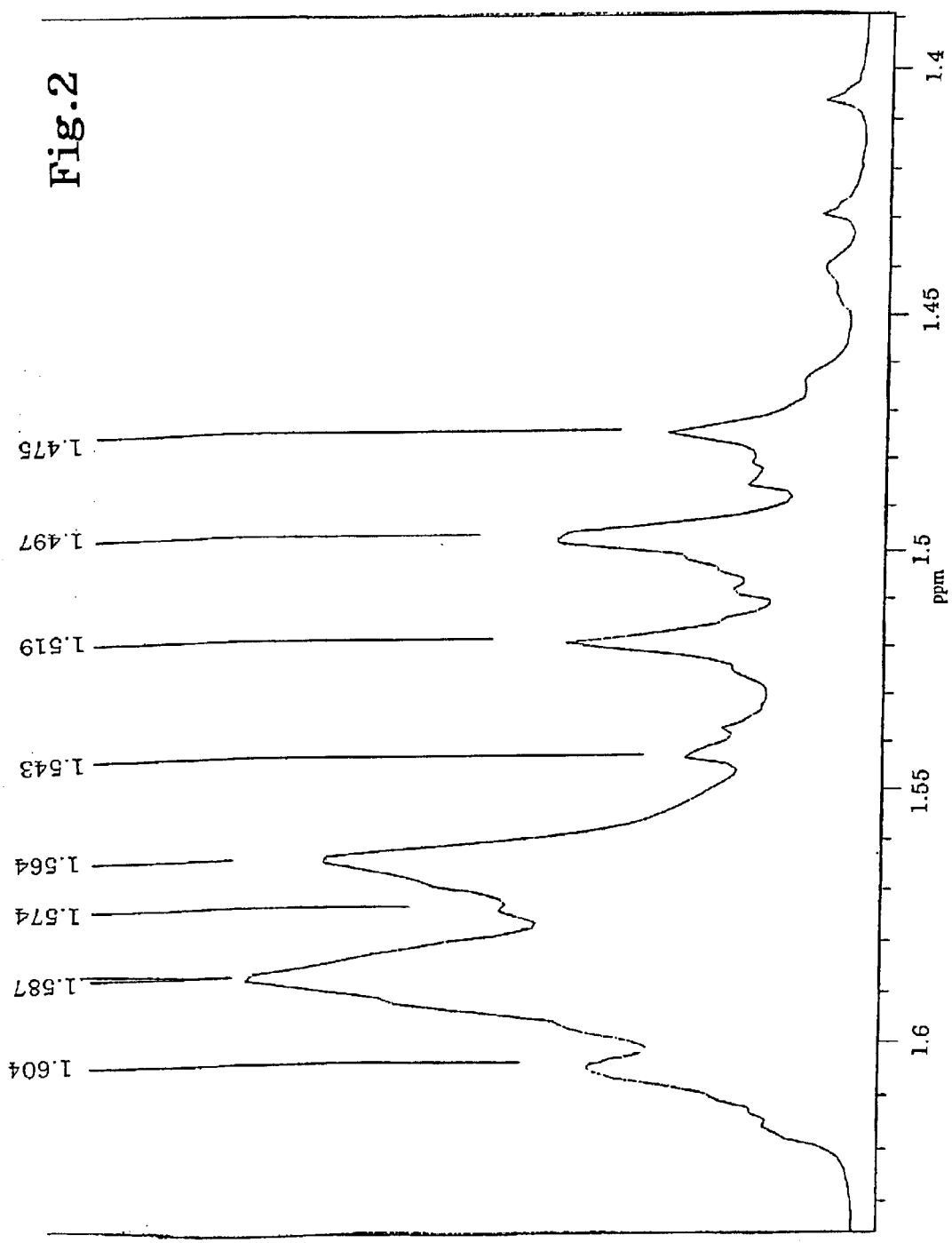
FIG. 2 shows a partial scale view of NMR of FIG. 1.
Figure 3:
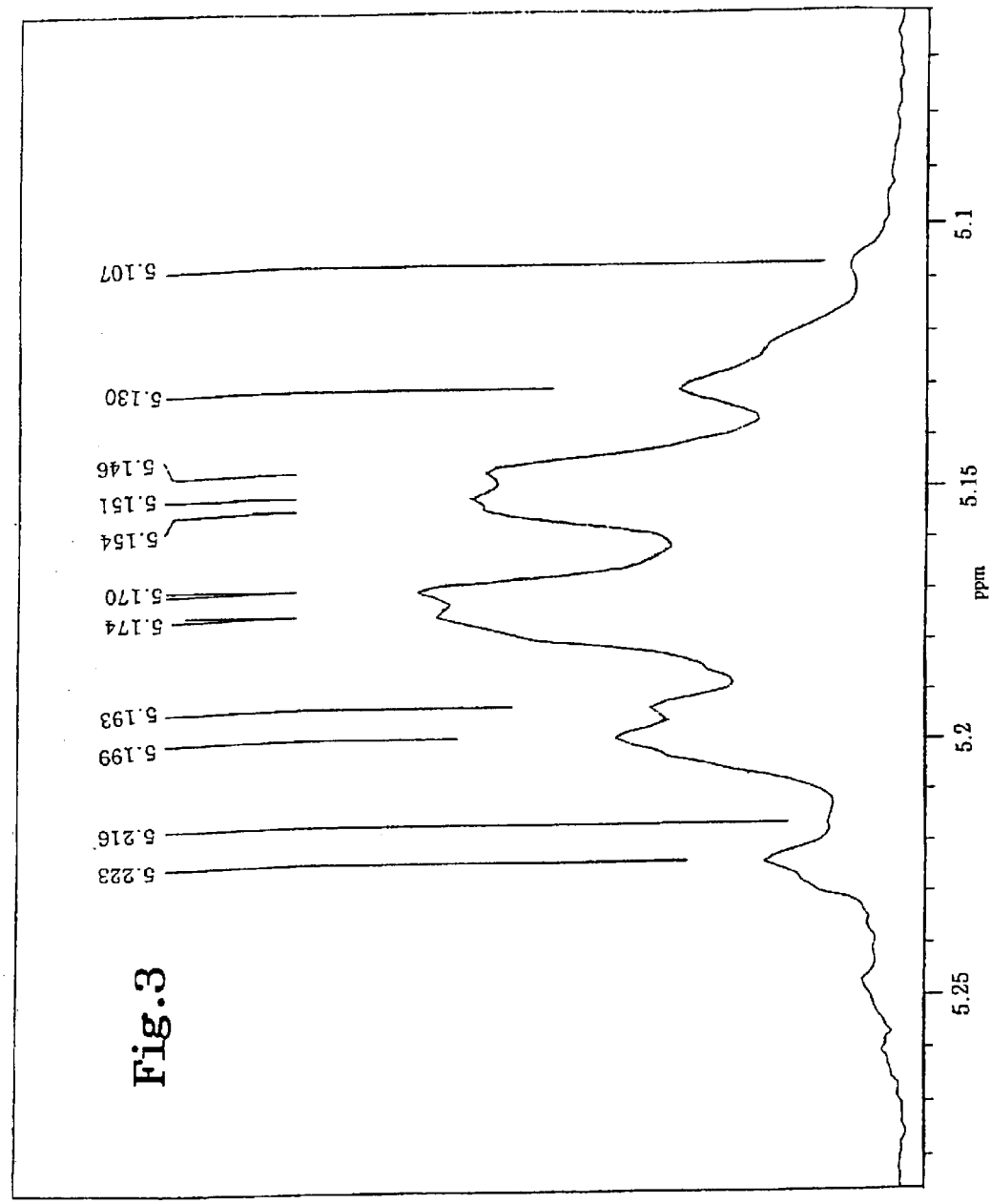
FIG. 3 shows a partial scale view of NMR of FIG. 1.

A general view of NMR of the product obtained in Example 1 is shown in FIG. 1, and scale views of a part of FIG. 1 are shown in FIGS. 2 and 3.

Example 2

A THF solution (2 ml) in which 0.054 g (1.17 mmol) of ethanol was dissolved was added to a 50 ml double-cap eggplant-shaped flask under a nitrogen atmosphere, and cooled to −78° C. in a dry ice/acetone bath. Then, 0.64 ml (1.00 mmol) of n-butyllithium was added thereto and the mixture was stirred for 15 minutes. Further, a THF solution (2 ml) in which 0.576 g (4.00 mmol) of (3R,6R)-(+)-3,6-dimethyl-1,4-dioxane-2,5-dione was dissolved was added thereto and stirred for 30 minutes.

After completion of stirring, 2 ml of saturated ammonium chloride was added to the mixture while maintaining a nitrogen atmosphere and 10 ml of water was further added thereto, and then the temperature was raised to room temperature by removal of the dry ice/acetone bath. Subsequently, the mixture was extracted with 20 ml of ether 8 times, and the ether layer was washed with 30 ml of saturated saline solution. Then, anhydrous sodium sulfate was added thereto and dried while stirring for 1 hour. The obtained product was subjected to vacuum concentration in which solvent was completely removed with a vacuum pump. As a result, 0.535 g (yield 84.9%) of product consisting of a mixture of cyclic oligo-lactate and chain oligo-lactate was obtained with a weight ratio between cyclic oligomer and chain oligomer being 82:18.

Figure 4:
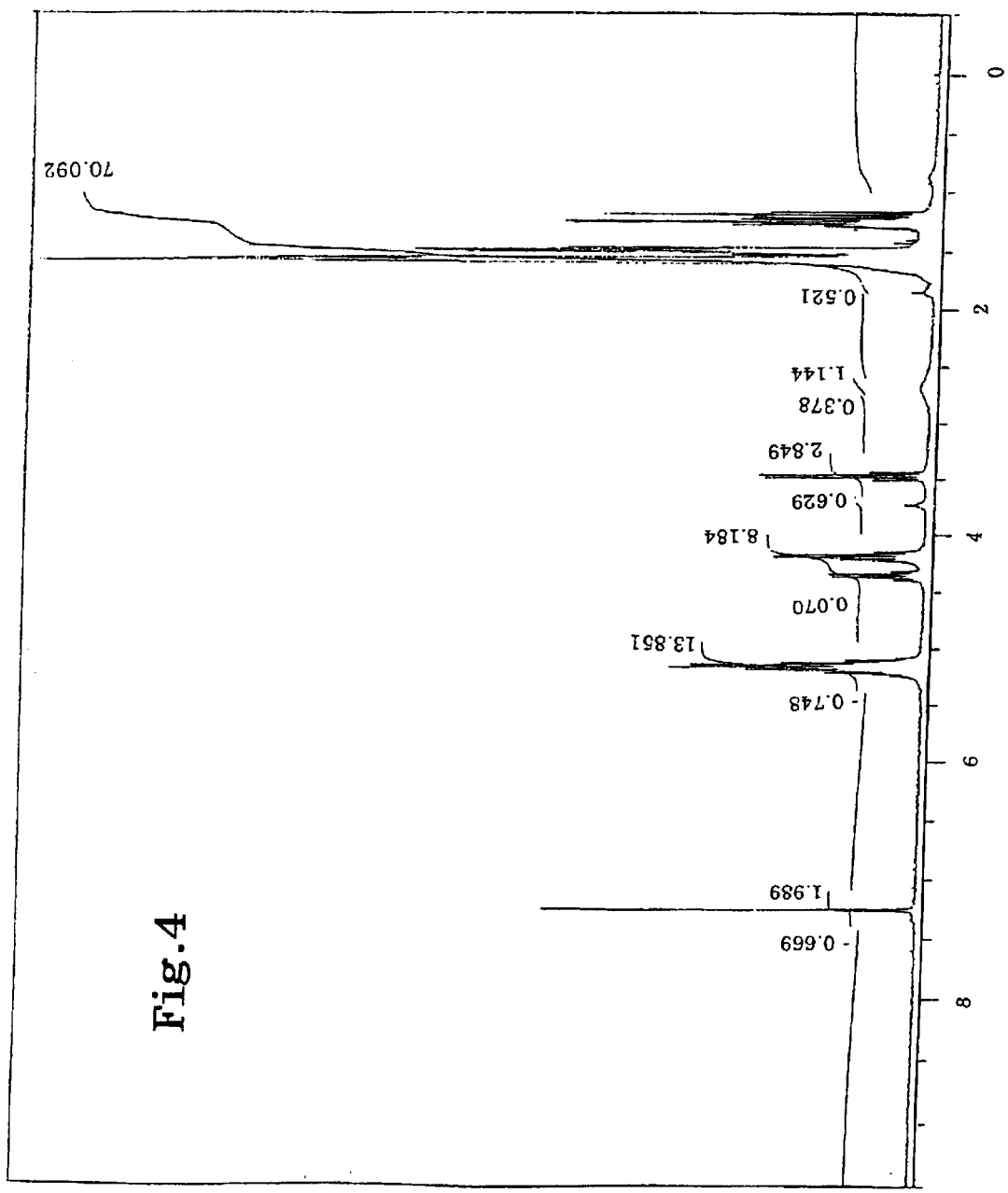
FIG. 4 shows a general view of NMR of the product obtained in Example 2.
Figure 5:
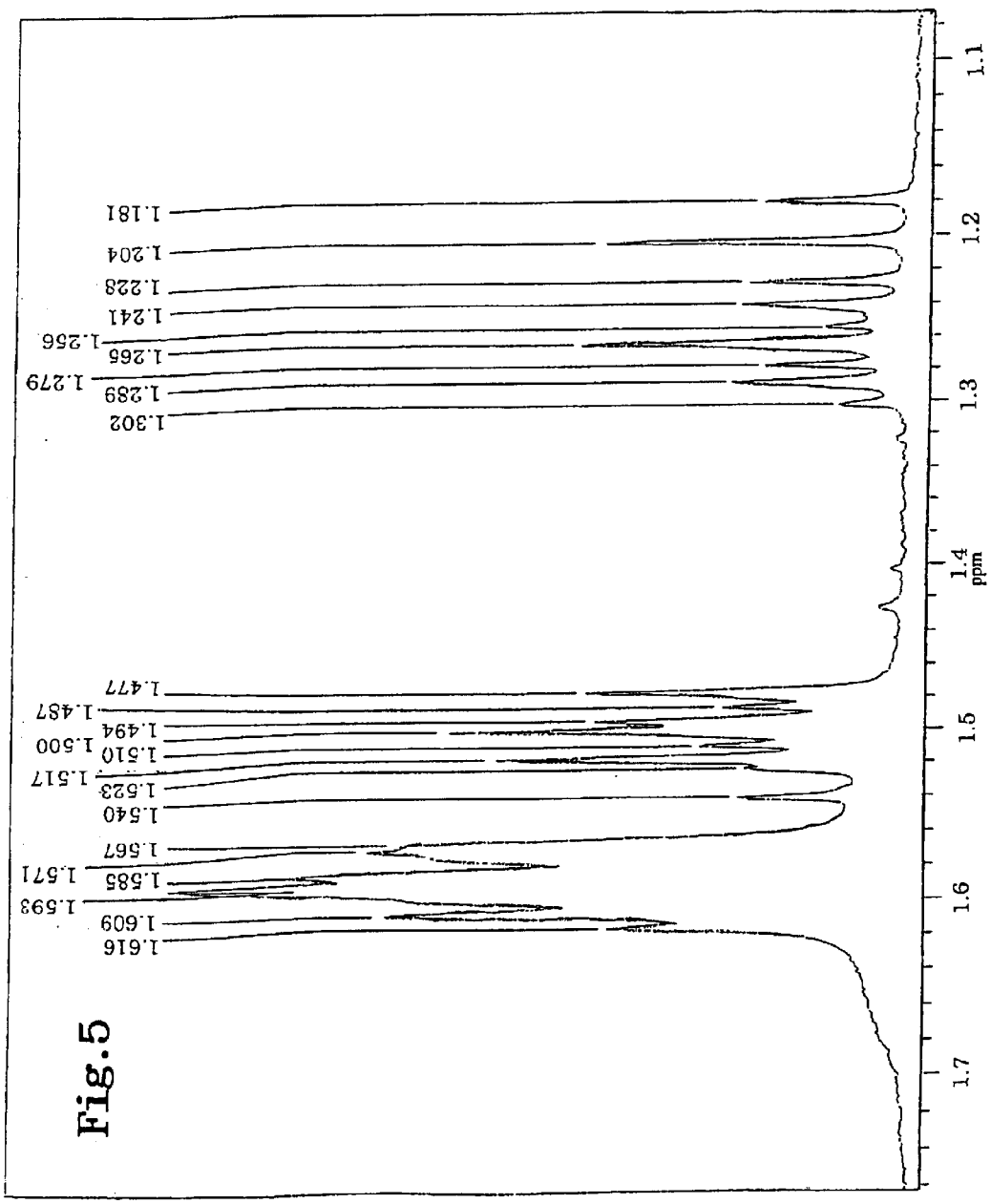
FIG. 5 shows a partial scale view of NMR of FIG. 4.
Figure 6:
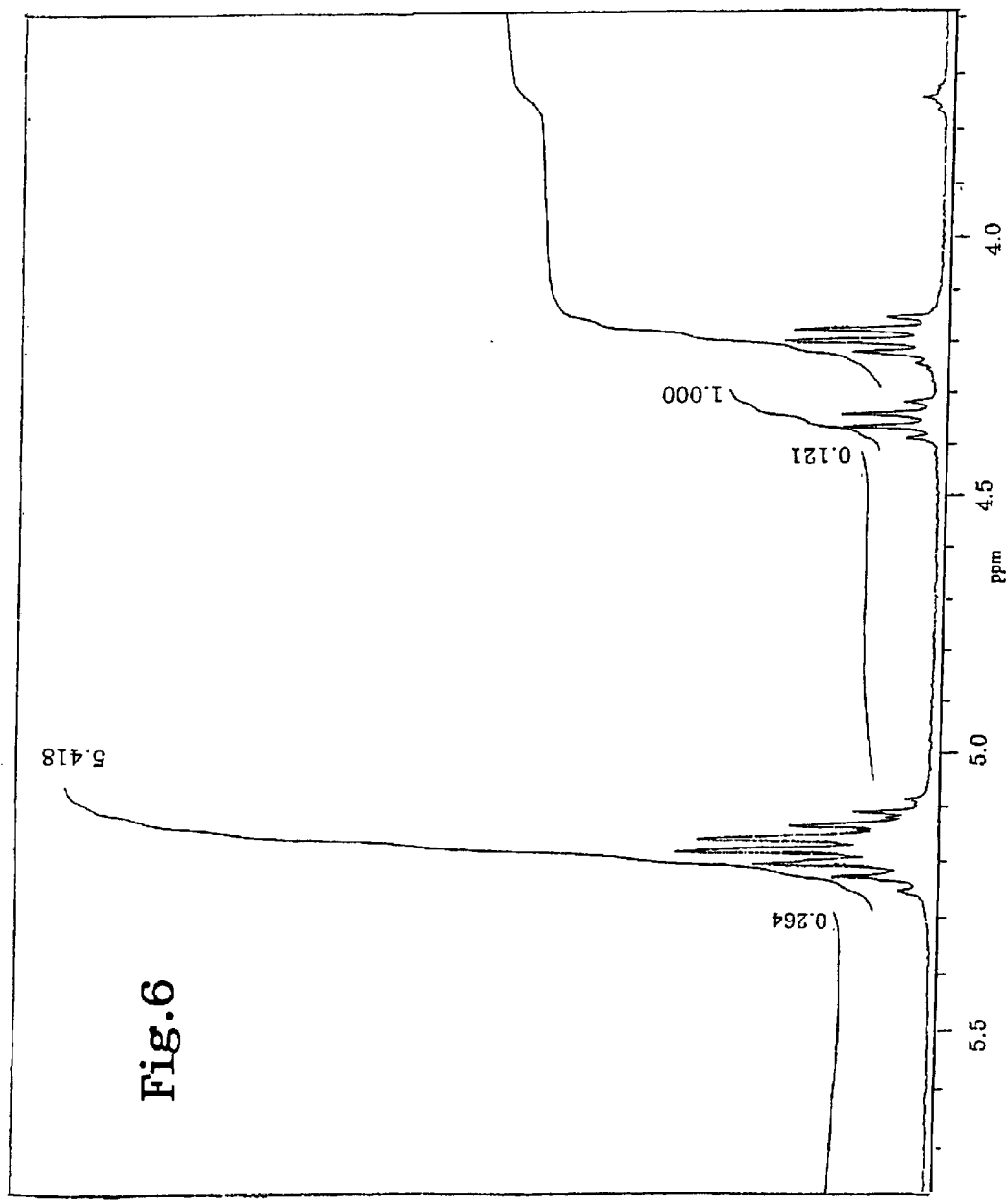
FIG. 6 shows a partial scale view of NMR of FIG. 4.

A general view of NMR of the product obtained in Example 2 is shown in FIG. 4 and scale views of a part of FIG. 4 are shown in FIGS. 5 and 6.

Example 3

A THF solution (2 ml) in which 0.062 g (1.03 mmol) of 2-propanol was dissolved was added to a 50 ml double-cap eggplant-shaped flask under a nitrogen atmosphere, and cooled to −78° C. in a dry ice/acetone bath. Then, 0.64 ml (1.00 mmol) of n-butyllithium was added thereto and the mixture was stirred for 15 minutes. Further, a THF solution (2 ml) in which 0.576 g (4.00 mmol) of (3R,6R)-(+)-3,6-dimethyl-1,4-dioxane-2,5-dione was dissolved was added thereto and stirred, and the temperature was gradually raised to room temperature over 4 hours.

After completion of stirring, 2 ml of saturated ammonium chloride was added to the mixture while maintaining a nitrogen atmosphere, and 10 ml of water was further added thereto. The mixture was extracted with chloroform and a saturated saline solution and washed, and then anhydrous sodium sulfate was added thereto and dried overnight. The obtained product was subjected to vacuum concentration in which solvent was completely removed with a vacuum pump. As a result, 0.589 g (yield 92.3%) of product consisting of a mixture of cyclic oligo-lactate and chain oligo-lactate was obtained with a weight ratio between cyclic oligomer and chain oligomer being 80:20.

Figure 7:
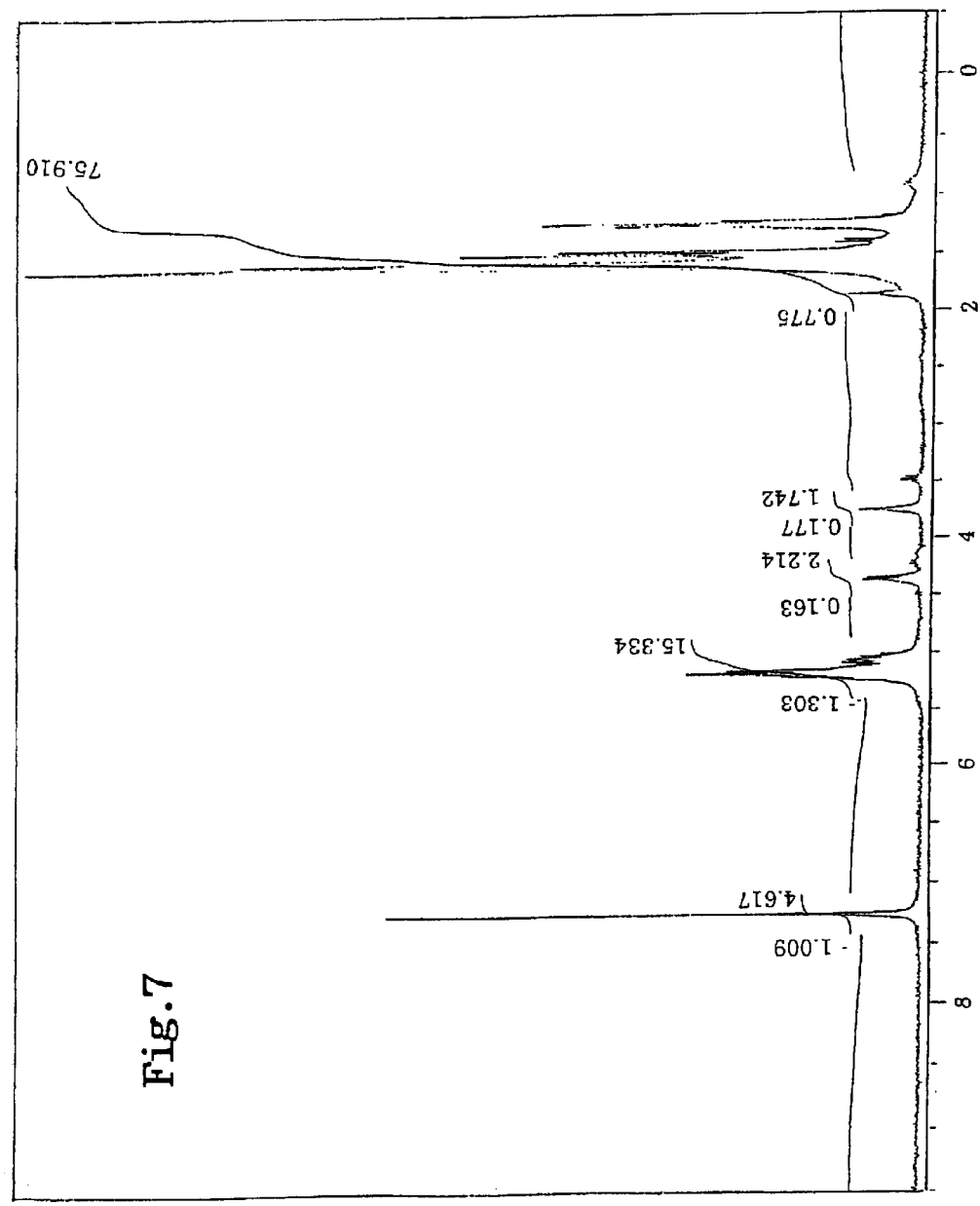
FIG. 7 shows a general view of NMR of the product obtained in Example 3.
Figure 8:
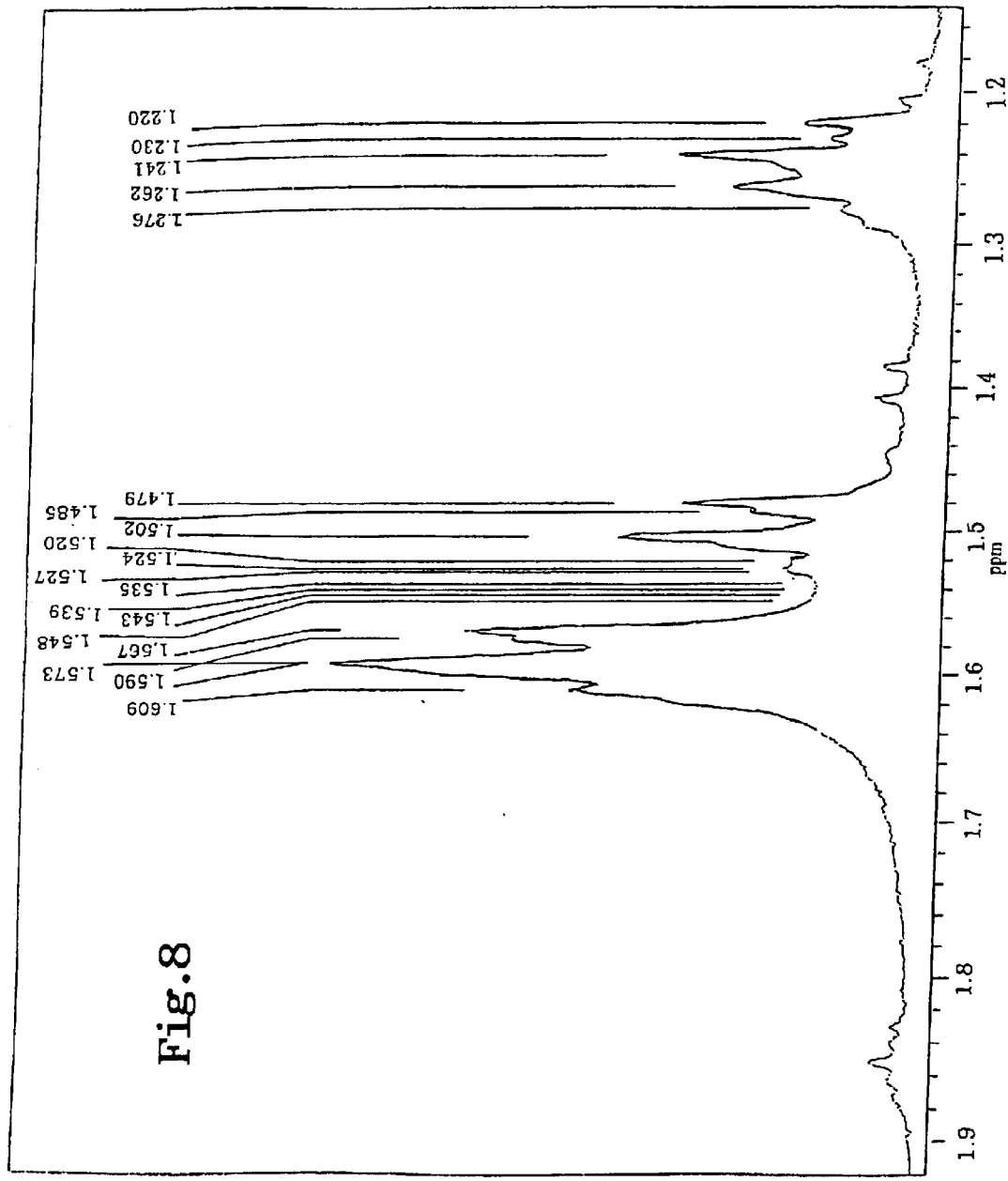
FIG. 8 shows a partial scale view of NMR of FIG. 7.
Figure 9:
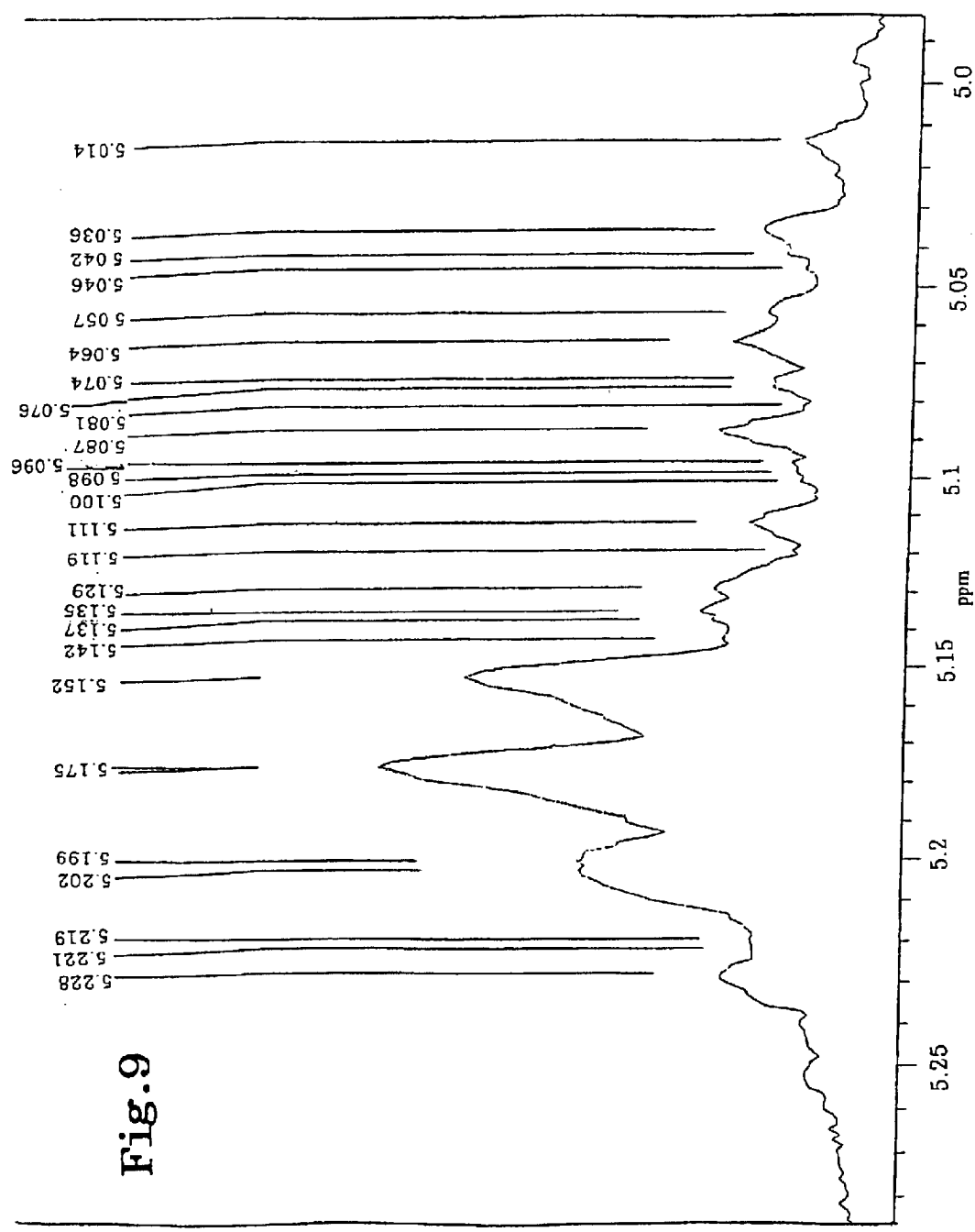
FIG. 9 shows a partial scale view of NMR of FIG. 7.

A general view of NMR of the product obtained in Example 3 is shown in FIG. 7, and scale views of a part of FIG. 7 are shown in FIGS. 8 and 9.

Example 4

A THF solution (2 ml) in which 0.074 g (1.00 mmol) of tert-butanol was dissolved was added to a 25 ml double-cap eggplant-shaped flask under a nitrogen atmosphere, and cooled to −78° C. in a dry ice/acetone bath. Then, 0.64 ml (1.00 mmol) of n-butyllithium was added thereto and the mixture was stirred for 15 minutes. Further, a THF solution (2 ml) in which 0.434 g (3.01 mmol) of (3R,6R)-(+)-3,6-dimethyl-1,4-dioxane-2,5-dione was dissolved was added thereto and stirred, and the temperature was gradually raised to room temperature over 2.5 hours.

After completion of stirring, 2 ml of saturated ammonium chloride was added to the mixture while maintaining a nitrogen atmosphere, and 10 ml of water was further added thereto. The mixture was extracted with chloroform and a saturated saline solution and washed, and then anhydrous sodium sulfate was added thereto and dried overnight. The obtained product was subjected to vacuum concentration in which solvent was completely removed with a vacuum pump. As a result, 0.537 g (yield 82.5%) of cyclic oligo-lactate wherein all asymmetric carbon atoms have an R configuration, was obtained.

Figure 10:
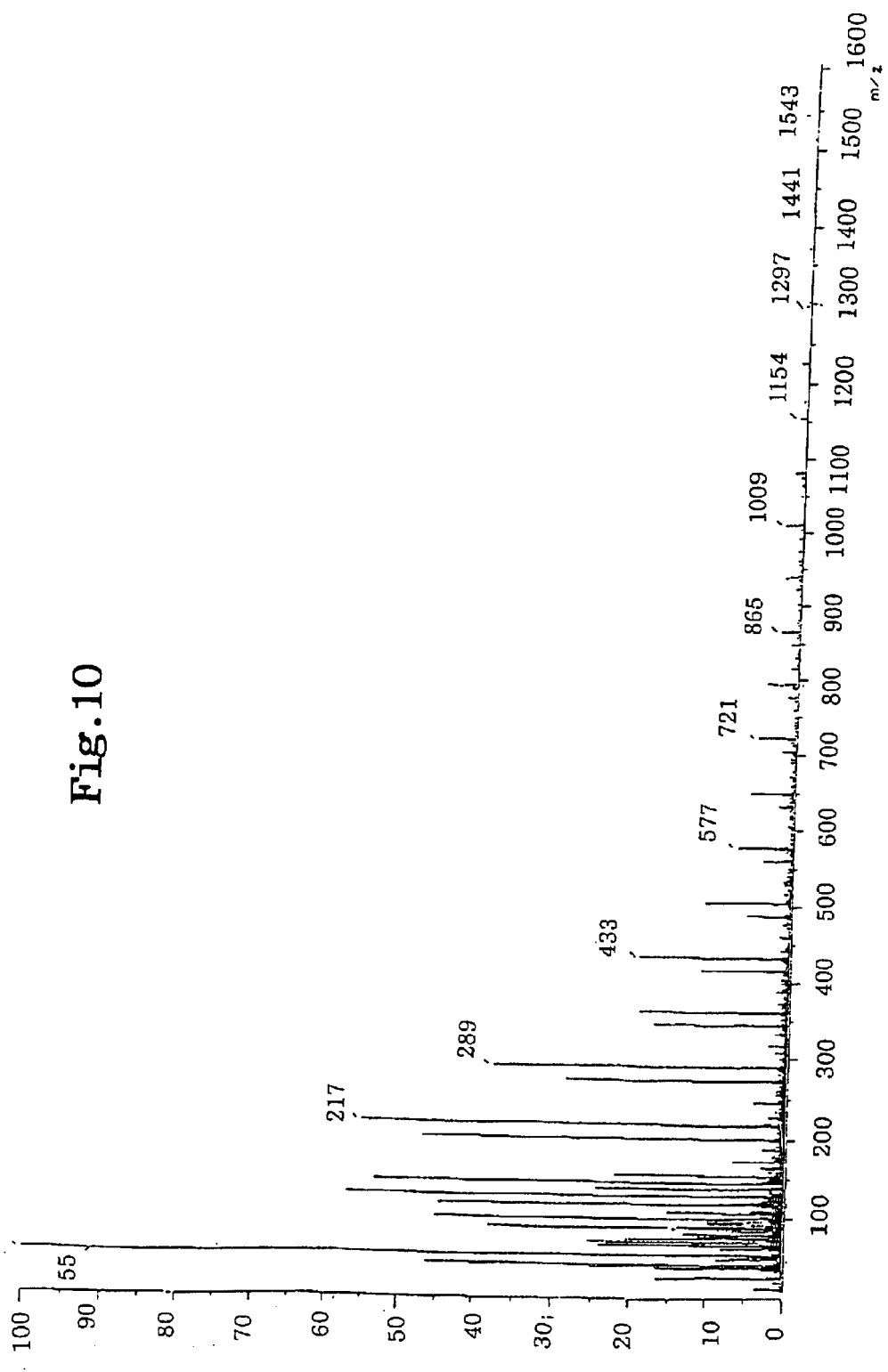
FIG. 10 shows an MS spectrum of the product obtained in Example 4.
Figure 11:
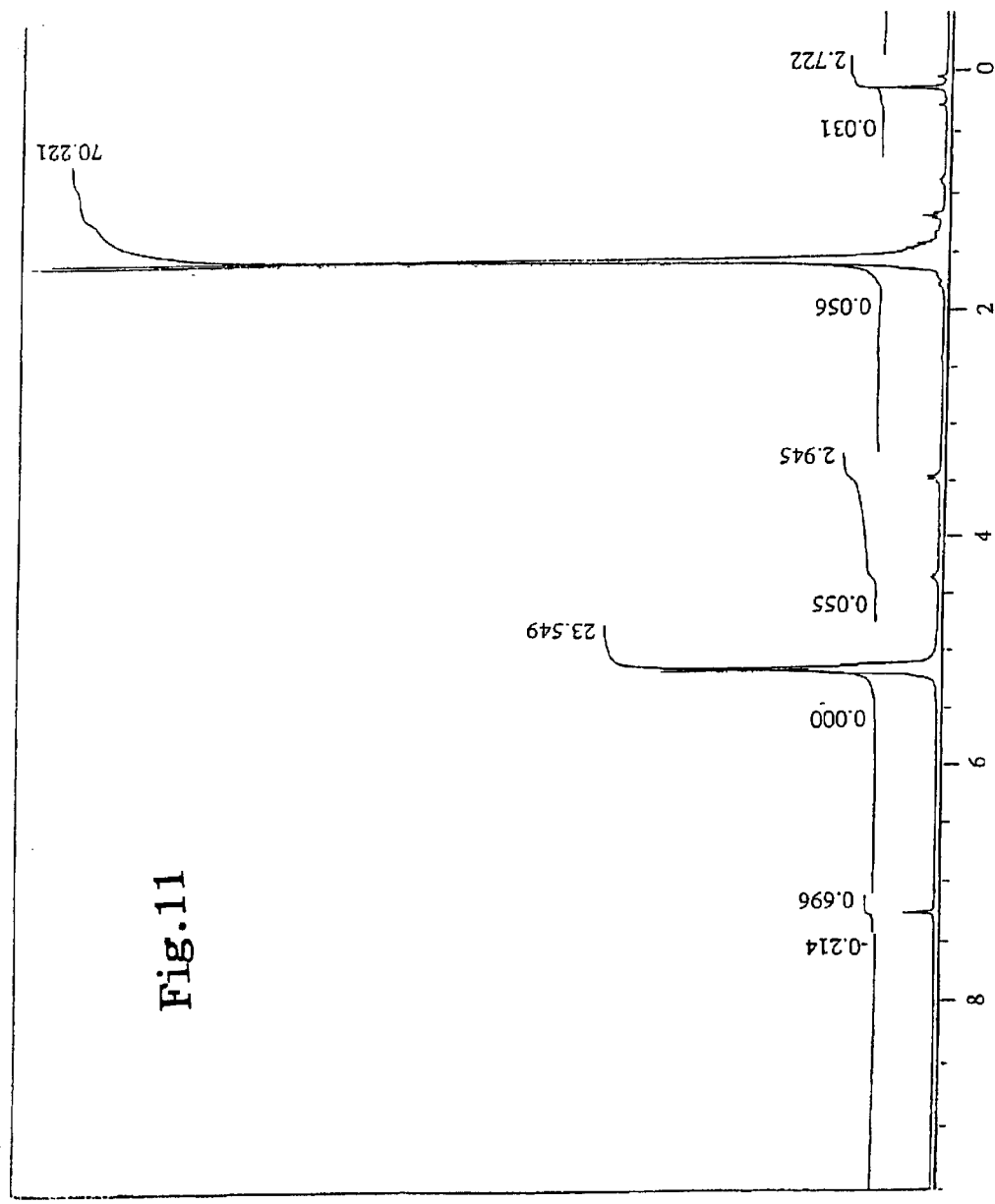
FIG. 11 shows a general view of NMR of the product obtained in Example 4.
Figure 12:
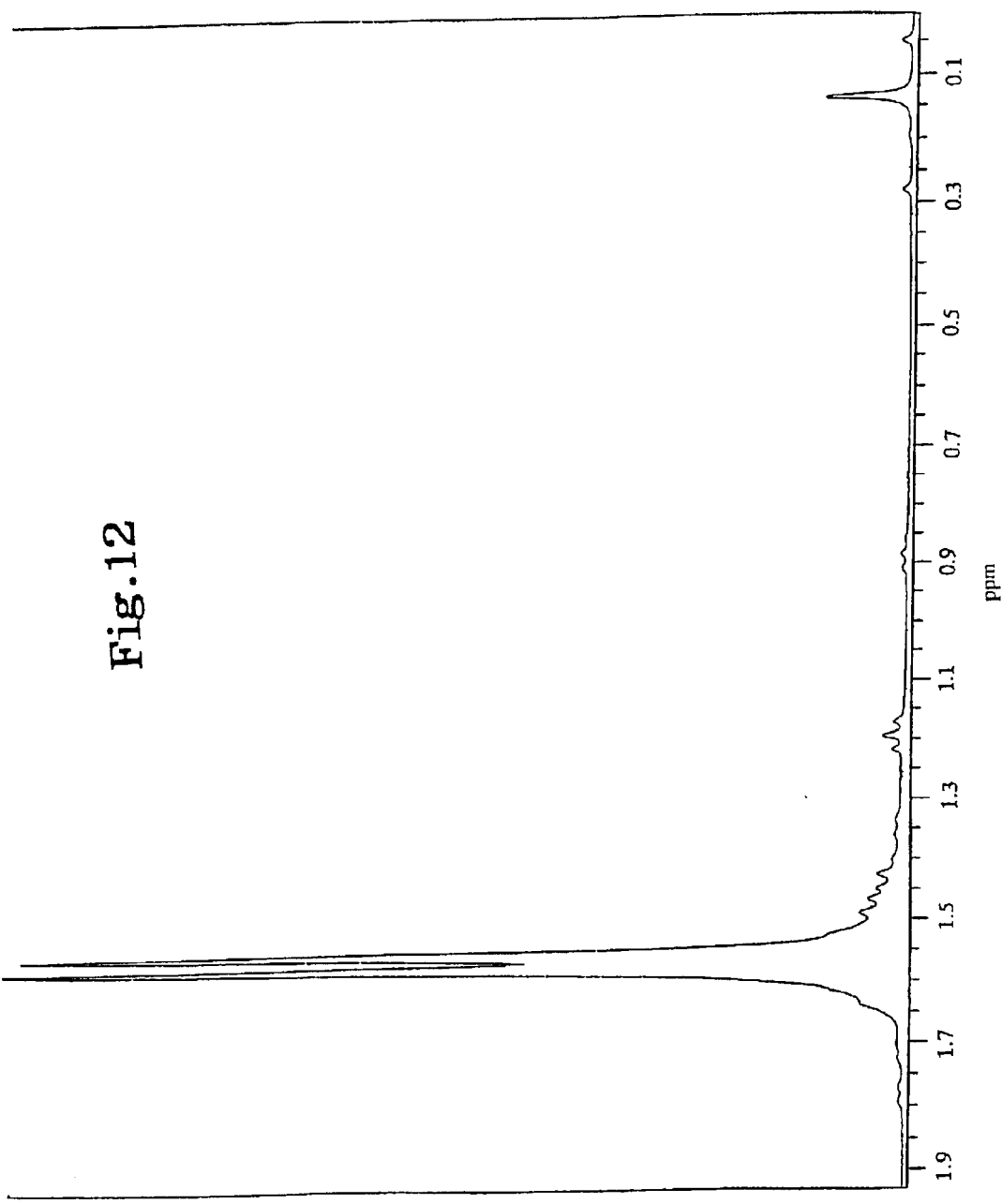
FIG. 12 shows a partial scale view of NMR of FIG. 11.
Figure 13:
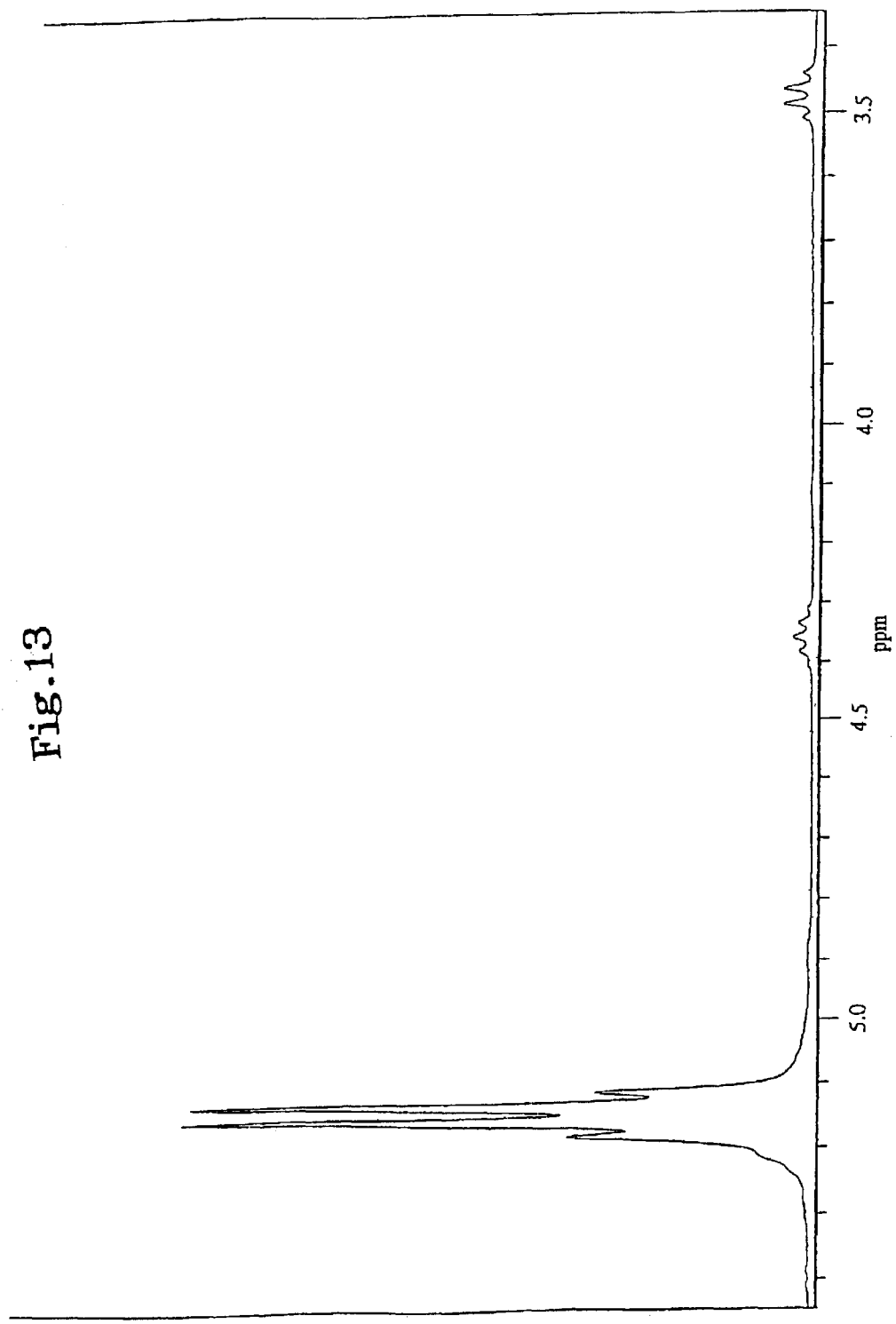
FIG. 13 shows a partial scale view of NMR of FIG. 11.

An MS spectrum of the product obtained in Example 4 is shown in FIG. 10. In addition, a general view of NMR of the product obtained in Example 4 is shown in FIG. 11, and scale views of a part of FIG. 11 are shown in FIGS. 12 and 13.

Example 5

A THF solution (2 ml) in which 0.117 g (1.06 mmol) of thiophenol was dissolved was added to a 50 ml double-cap eggplant-shaped flask under a nitrogen atmosphere, and cooled to −78° C. in a dry ice/acetone bath. Then, 0.64 ml (1.00 mmol) of n-butyllithium was added thereto and the mixture was stirred for 15 minutes. Further, a THF solution (2 ml) in which 0.576 g (4.00 mmol) of (3R,6R)-(+)-3,6-dimethyl-1,4-dioxane-2,5-dione was dissolved was added thereto and stirred, and the temperature was gradually raised to room temperature over 4 hours.

After completion of stirring, 2 ml of saturated ammonium chloride was added to the mixture while maintaining a nitrogen atmosphere, and 10 ml of water was further added thereto. The mixture was extracted with chloroform and a saturated saline solution and washed, and then anhydrous sodium sulfate was added thereto and dried overnight. The obtained product was subjected to vacuum concentration in which solvent was completely removed with a vacuum pump. As a result, 0.612 g (yield 88.3%) of product was obtained. It was confirmed by NMR analysis that this product comprised cyclic oligo-lactate and chain oligo-lactate at a weight ratio of 96:4.

0.238 g of the product was isolated and purified using silica gel chromatography (solvent; hexane:ether=1:2) to obtain 5 fractions (fraction Nos. 10-1 to 10-5).

Figure 14:
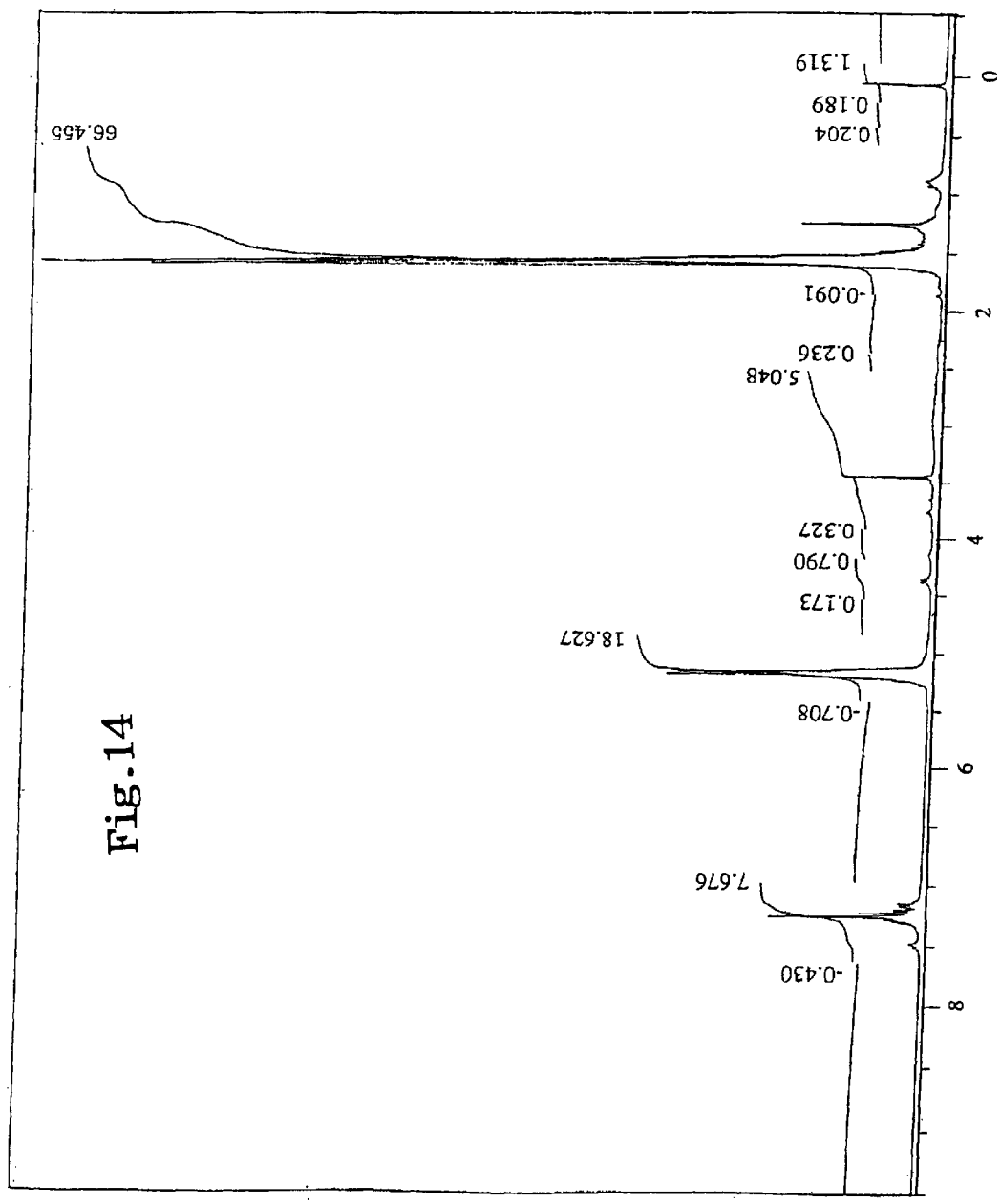
FIG. 14 shows a general view of NMR of the product obtained in Example 5.
Figure 15:
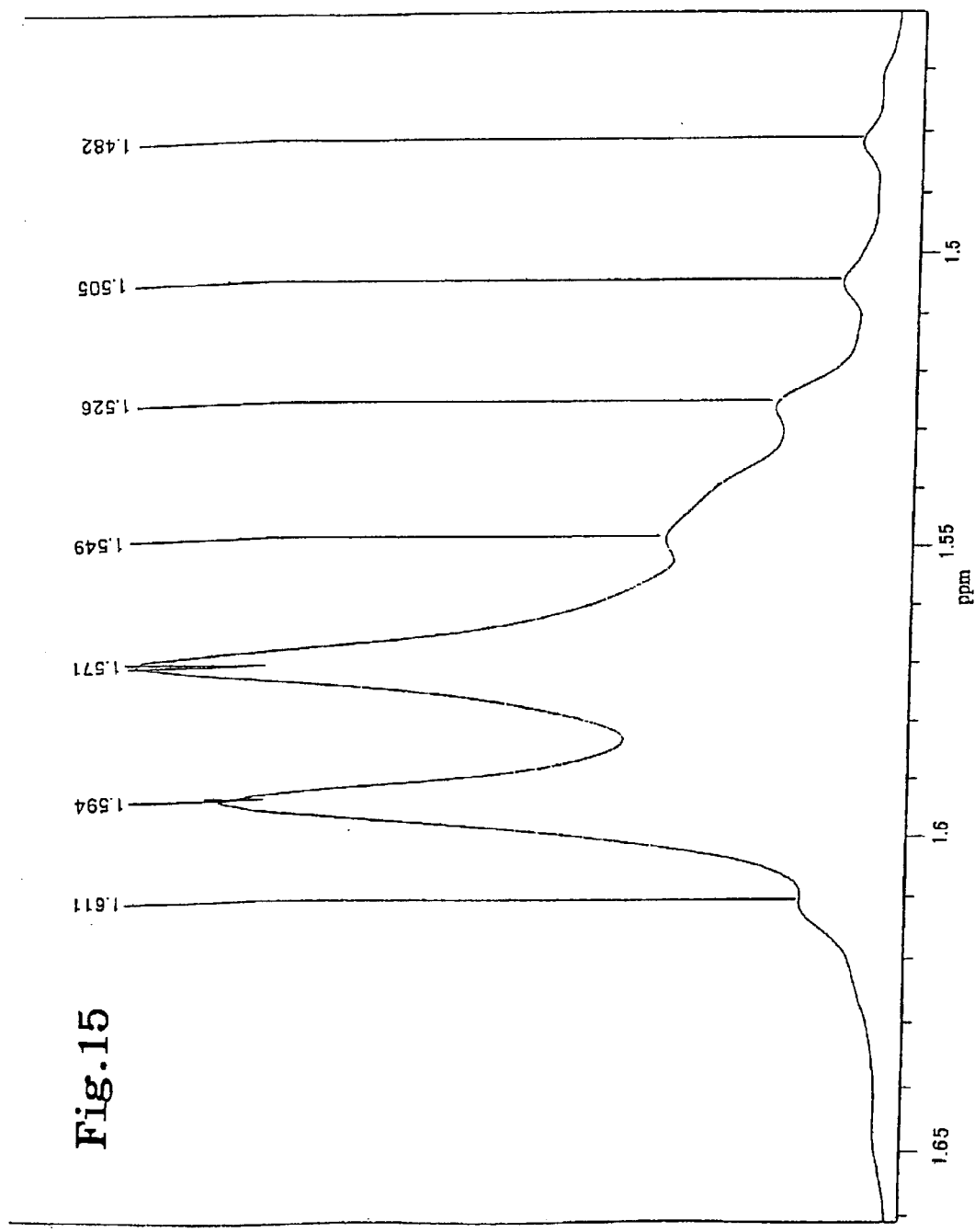
FIG. 15 shows a partial scale view of NMR of FIG. 14.
Figure 16:
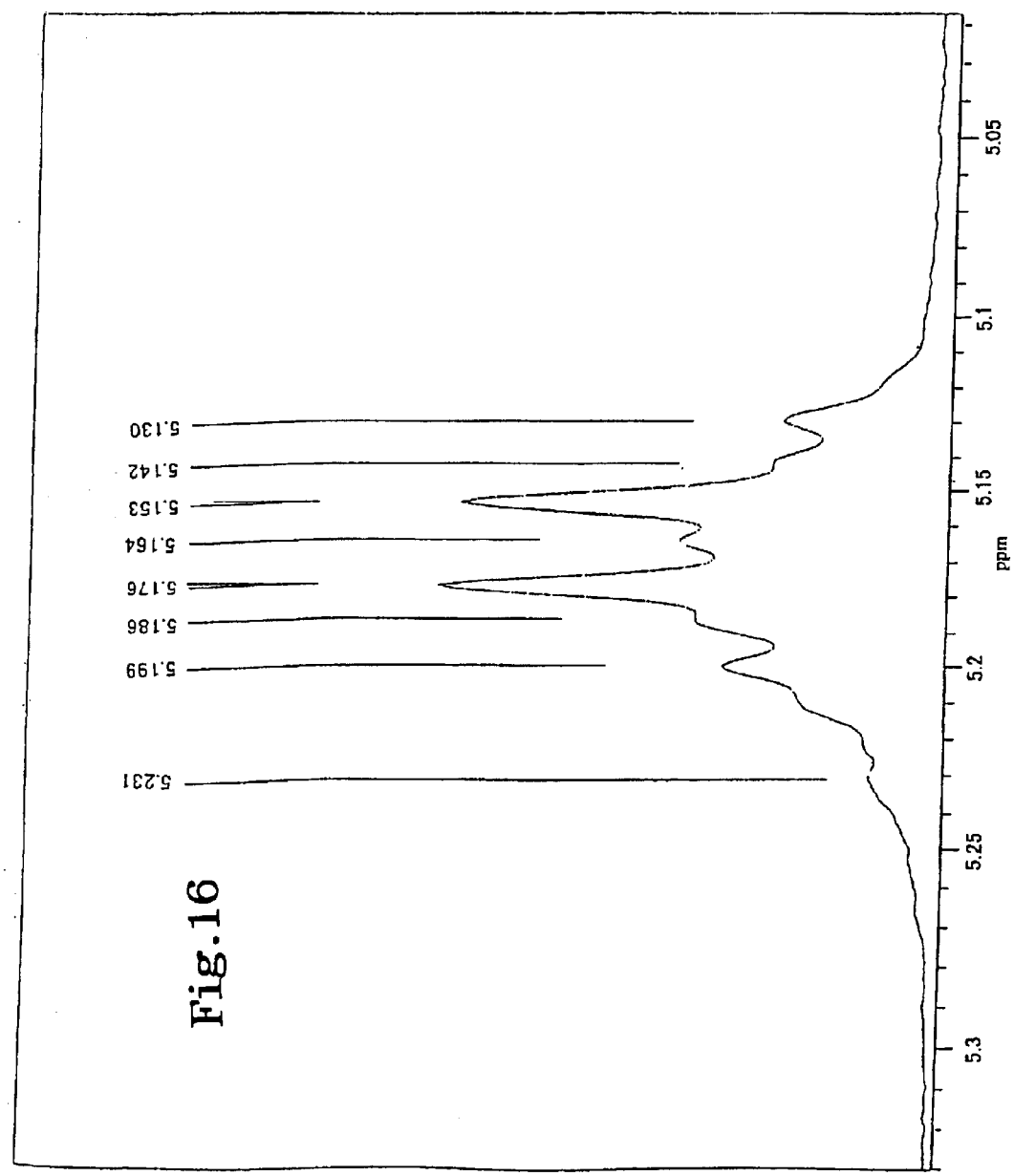
FIG. 16 shows a partial scale view of NMR of FIG. 14.

A general view of NMR of the product obtained in Example 5 is shown in FIG. 14, and scale views of a part of FIG. 14 are shown in FIGS. 15 and 16.

Example 6

3 ml of THF solution containing 0.089 g (1 mmol) of S-lactic acid amide was added to a 50 ml double-cap eggplant-shaped flask at room temperature under a nitrogen atmosphere, and 0.64 ml (1.00 mmol) of n-butyllithium was reacted therewith at −78° C. followed by stirring for 15 minutes. Further, 2 ml of THF solution containing 0.576 g (4 mmol) of L-(−)-lactide was added thereto and reacted therewith for 30 minutes, and then the temperature was raised from −78° C. to 0° C. followed by reaction for 1.5 hours. Subsequently, the temperature was further raised to room temperature by addition of 5 ml of saturated ammonium chloride solution. After the mixture was extracted with chloroform, the organic layer was washed with a saturated saline solution, and dried with anhydrous sodium sulfate followed by vacuum concentration (NMR sa0140), to obtain a residue.

Figure 17:
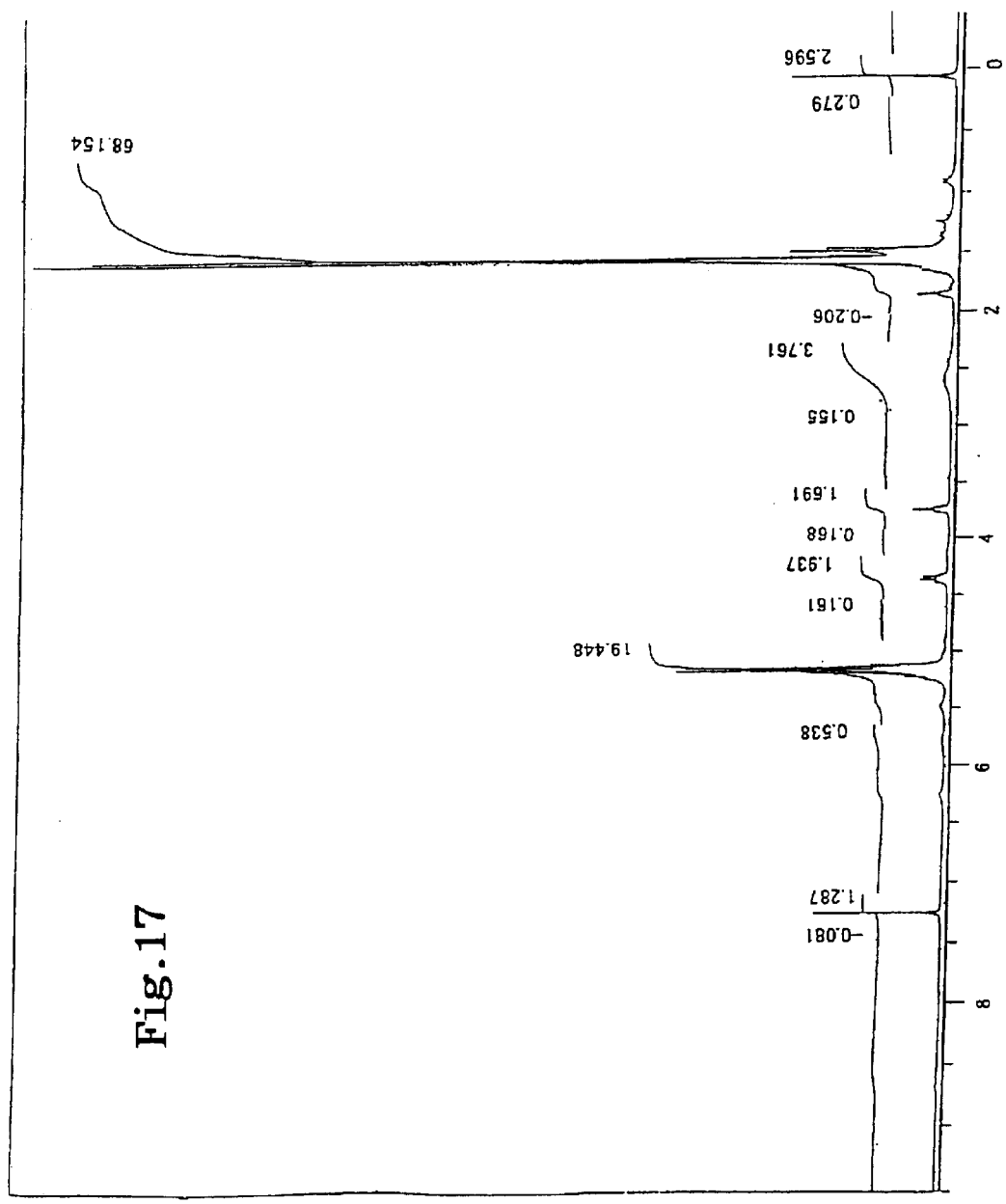
FIG. 17 shows a general view of NMR of the product obtained in Example 6.
Figure 18:
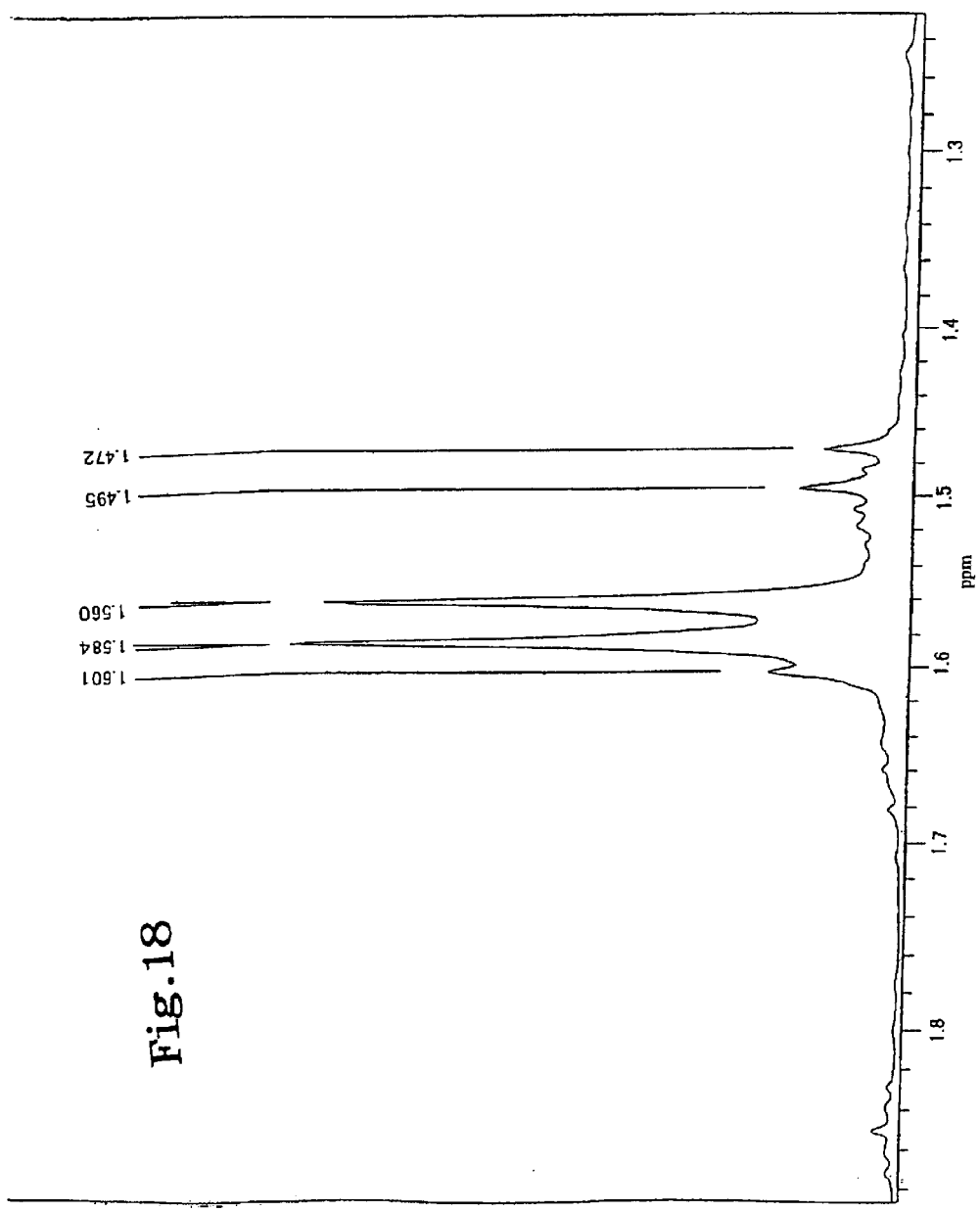
FIG. 18 shows a partial scale view of NMR of FIG. 17.
Figure 19:
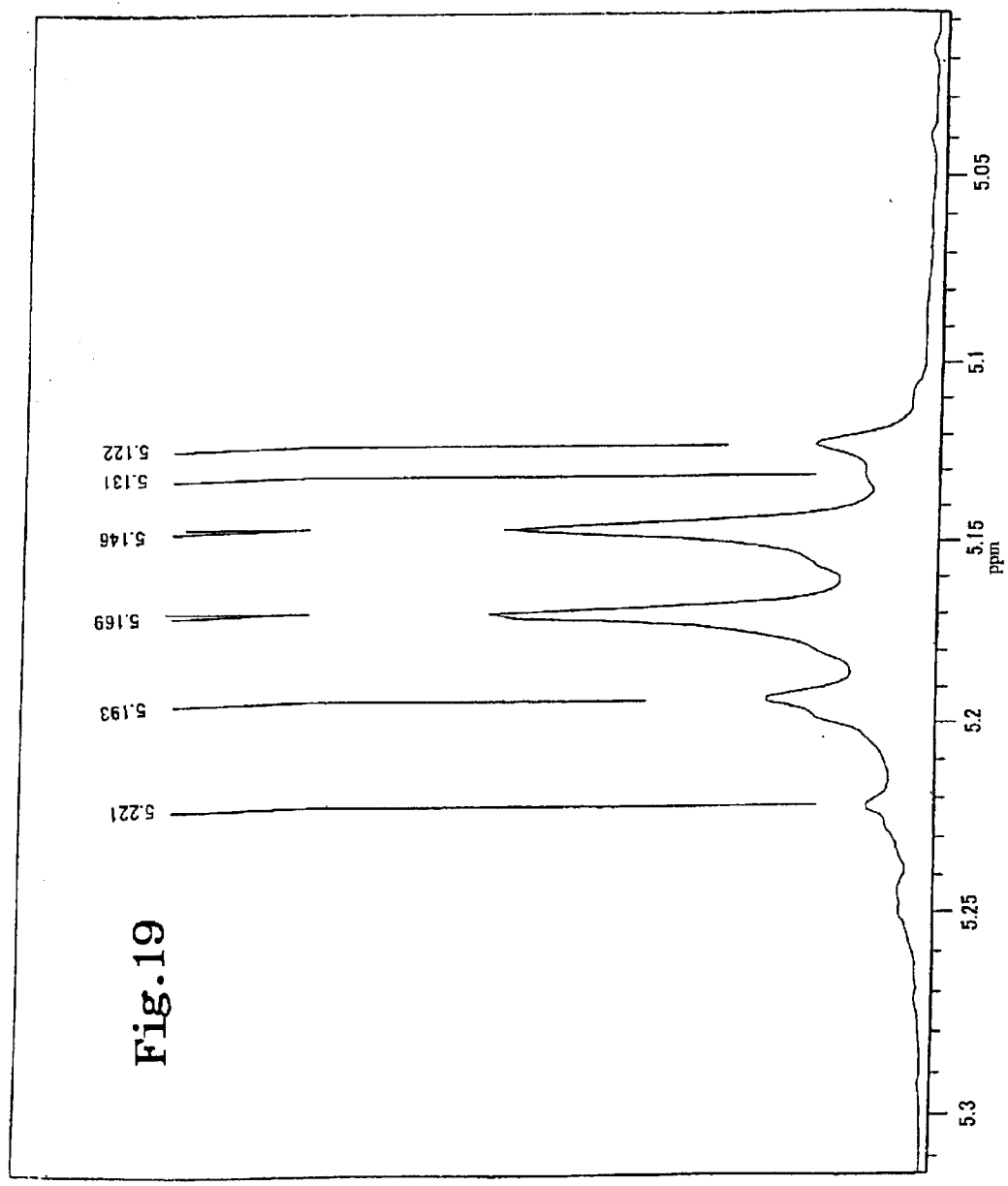
FIG. 19 shows a partial scale view of NMR of FIG. 17.

A general view of NMR of the product obtained in Example 6 is shown in FIG. 17, and scale views of a part of FIG. 17 are shown in FIGS. 18 and 19.

Example 7

A THF solution (2 ml) in which 0.090 g (1.00 mmol) of trimethylsilanol was dissolved was added to a 25 ml double-cap eggplant-shaped flask under a nitrogen atmosphere, and cooled to 0° C. Then, 0.64 ml (1.00 mmol) of n-butyllithium was added thereto and the mixture was stirred for 15 minutes. Further, a THF solution (2 ml) in which 0.434 g (3.01 mmol) of (3R,6R)-(+)-3,6-dimethyl-1,4-dioxane-2,5-dione was dissolved was added thereto and stirred, and the temperature was gradually raised to room temperature over 2.5 hours.

After completion of stirring, 2 ml of saturated ammonium chloride was added to the mixture while maintaining a nitrogen atmosphere, and 10 ml of water was further added thereto. The mixture was extracted with chloroform and a saturated saline solution and washed, and then anhydrous sodium sulfate was added thereto and dried overnight. The obtained product was subjected to vacuum concentration in which solvent was completely removed with a vacuum pump. As a result, 0.537 g (yield 82.5%) of cyclic oligo-lactate wherein all asymmetric carbon atoms have an R configuration, was obtained.

Figure 20:
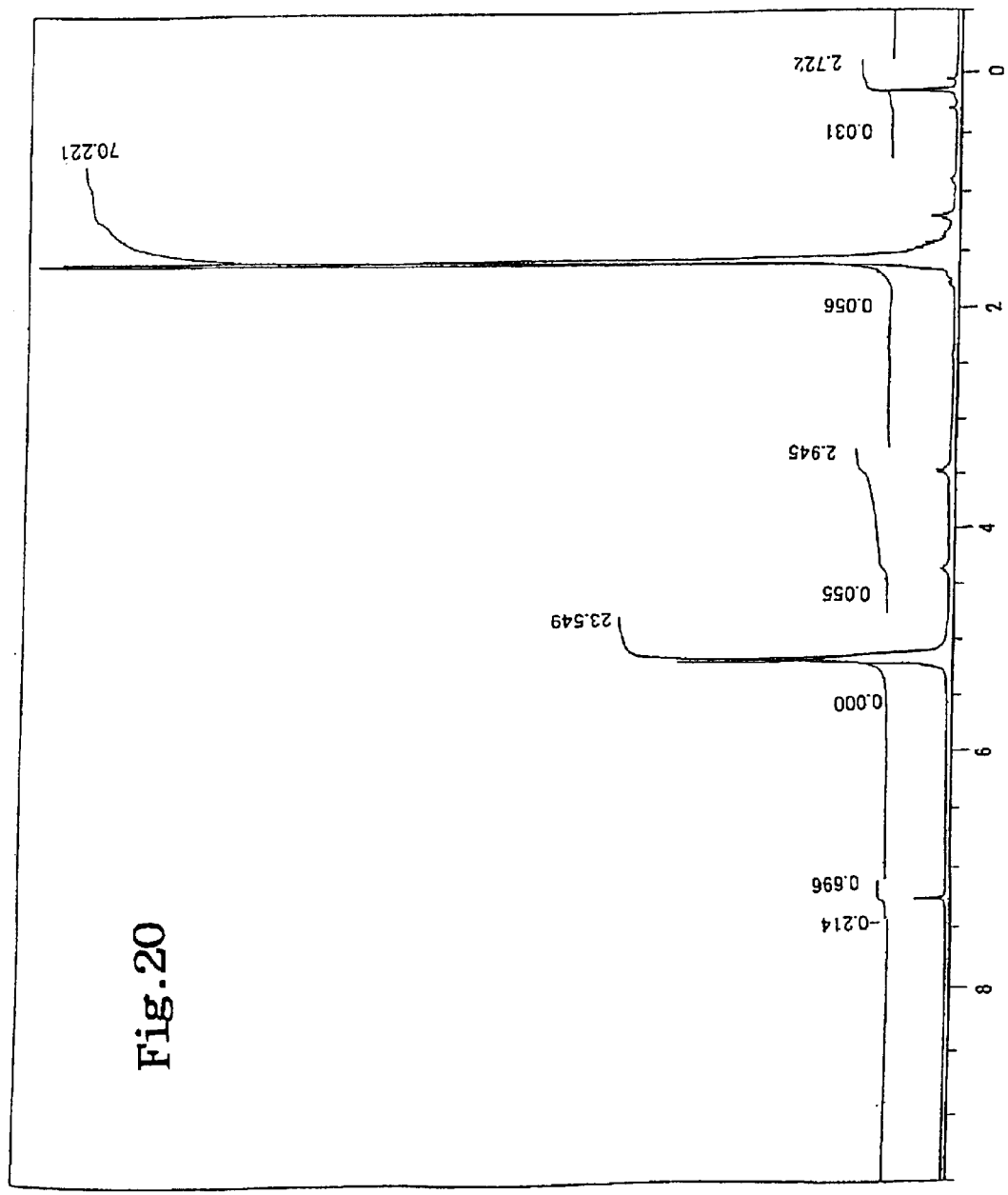
FIG. 20 shows a general view of NMR of the product obtained in Example 7.
Figure 21:
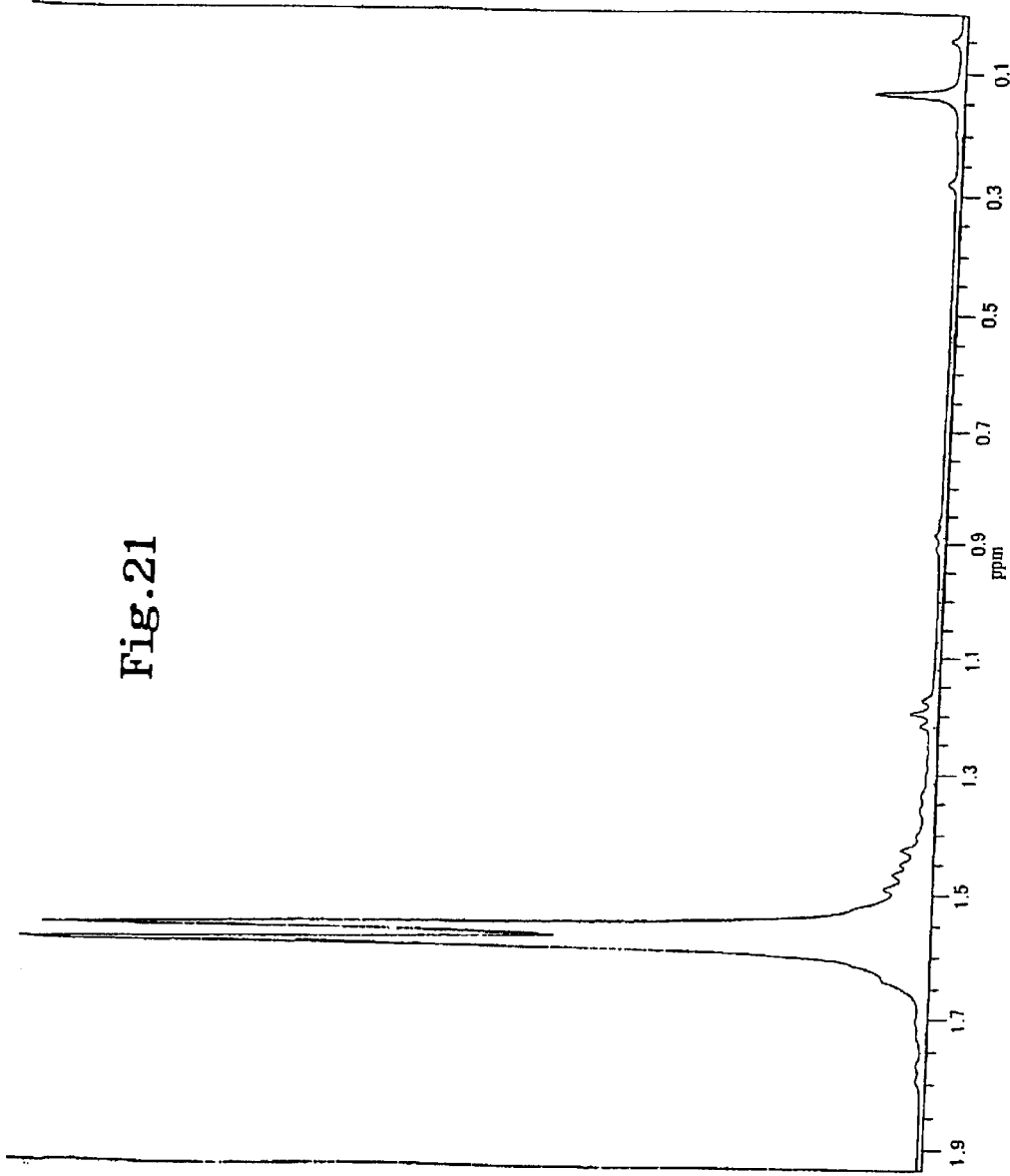
FIG. 21 shows a partial scale view of NMR of FIG. 20.
Figure 22:
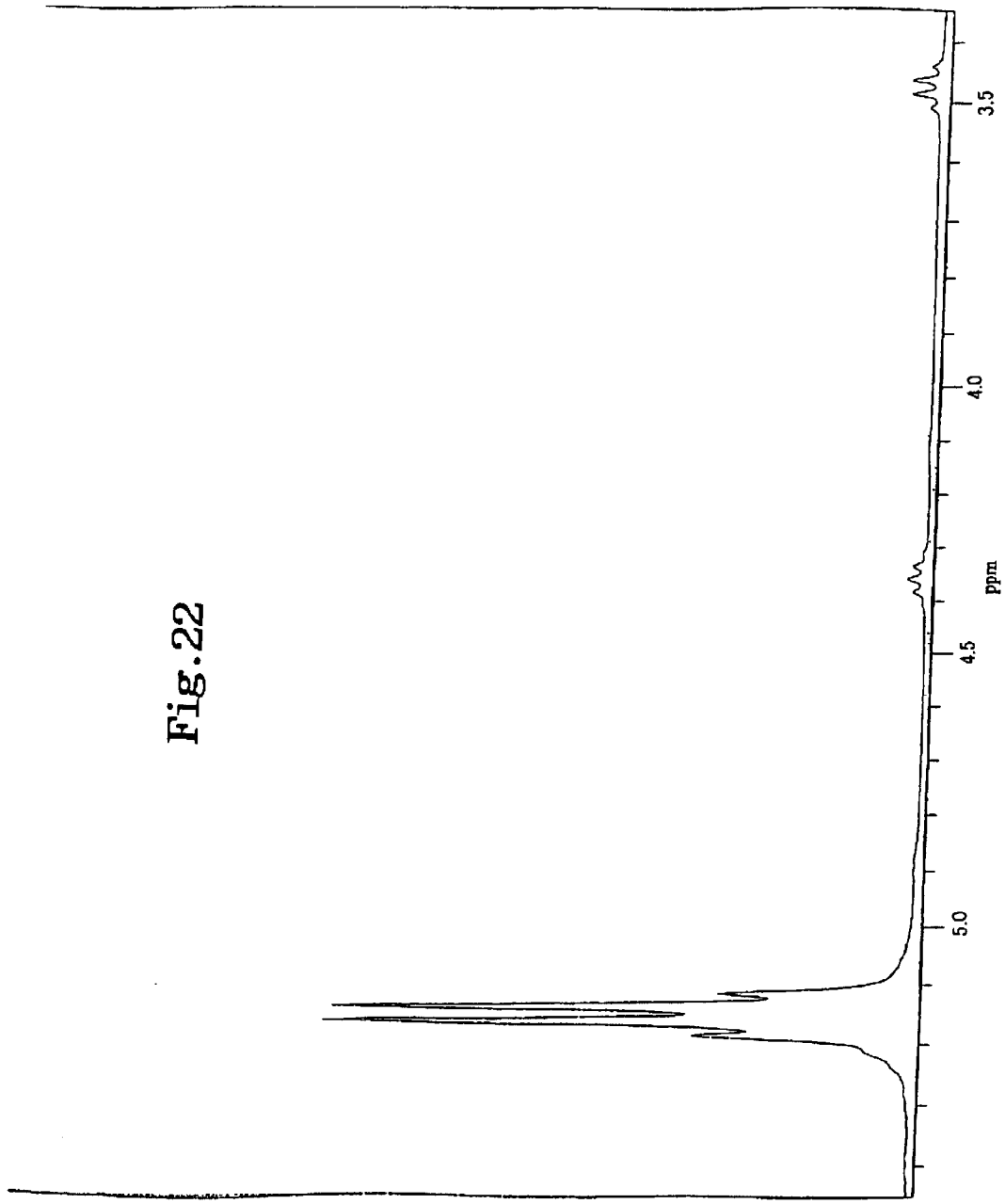
FIG. 22 shows a partial scale view of NMR of FIG. 20.

A general view of NMR of the product obtained in Example 7 is shown in FIG. 20, and scale views of a part of FIG. 20 are shown in FIGS. 21 and 22.

Example 8

A THF solution (2 ml) in which 0.276 g (1.00 mmol) of triphenylsilanol was dissolved was added to a 25 ml double-cap eggplant-shaped flask under a nitrogen atmosphere, and cooled to 0° C. Then, 0.64 ml (1.00 mmol) of n-butyllithium was added thereto and the mixture was stirred for 15 minutes. Further, a THF solution (2 ml) in which 0.434 g (3.01 mmol) of (3R,6R)-(+)-3,6-dimethyl-1,4-dioxane-2,5-dione was dissolved was added thereto and stirred, and the temperature was gradually raised to room temperature over 2.5 hours.

After completion of stirring, 2 ml of saturated ammonium chloride was added to the mixture while maintaining a nitrogen atmosphere, and 10 ml of water was further added thereto. The mixture was extracted with chloroform and a saturated saline solution and washed, and then anhydrous sodium sulfate was added thereto and dried overnight. The obtained product was subjected to vacuum concentration in which solvent was completely removed with a vacuum pump. As a result, 0.537 g (yield 82.5%) of cyclic oligo-lactate wherein all asymmetric carbon atoms have an R configuration, was obtained.

Figure 23:
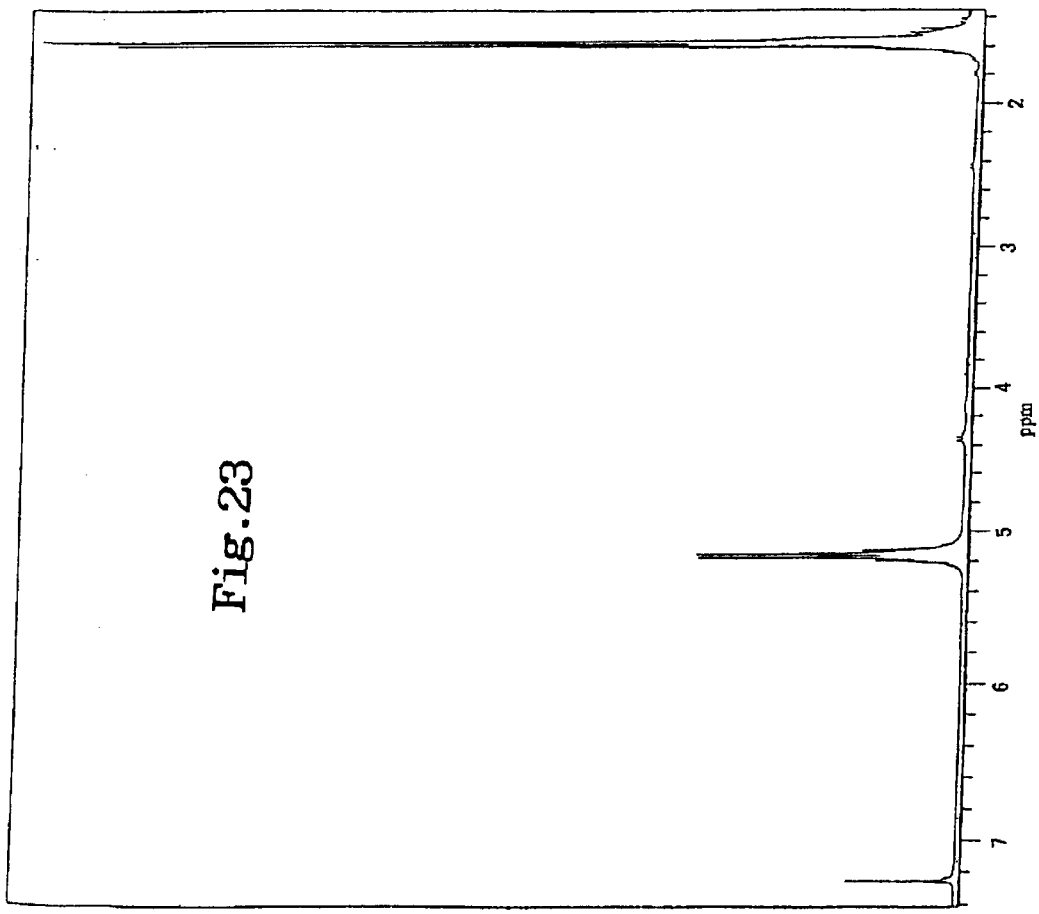
FIG. 23 shows a general view of NMR of the product obtained in Example 8.
Figure 24:
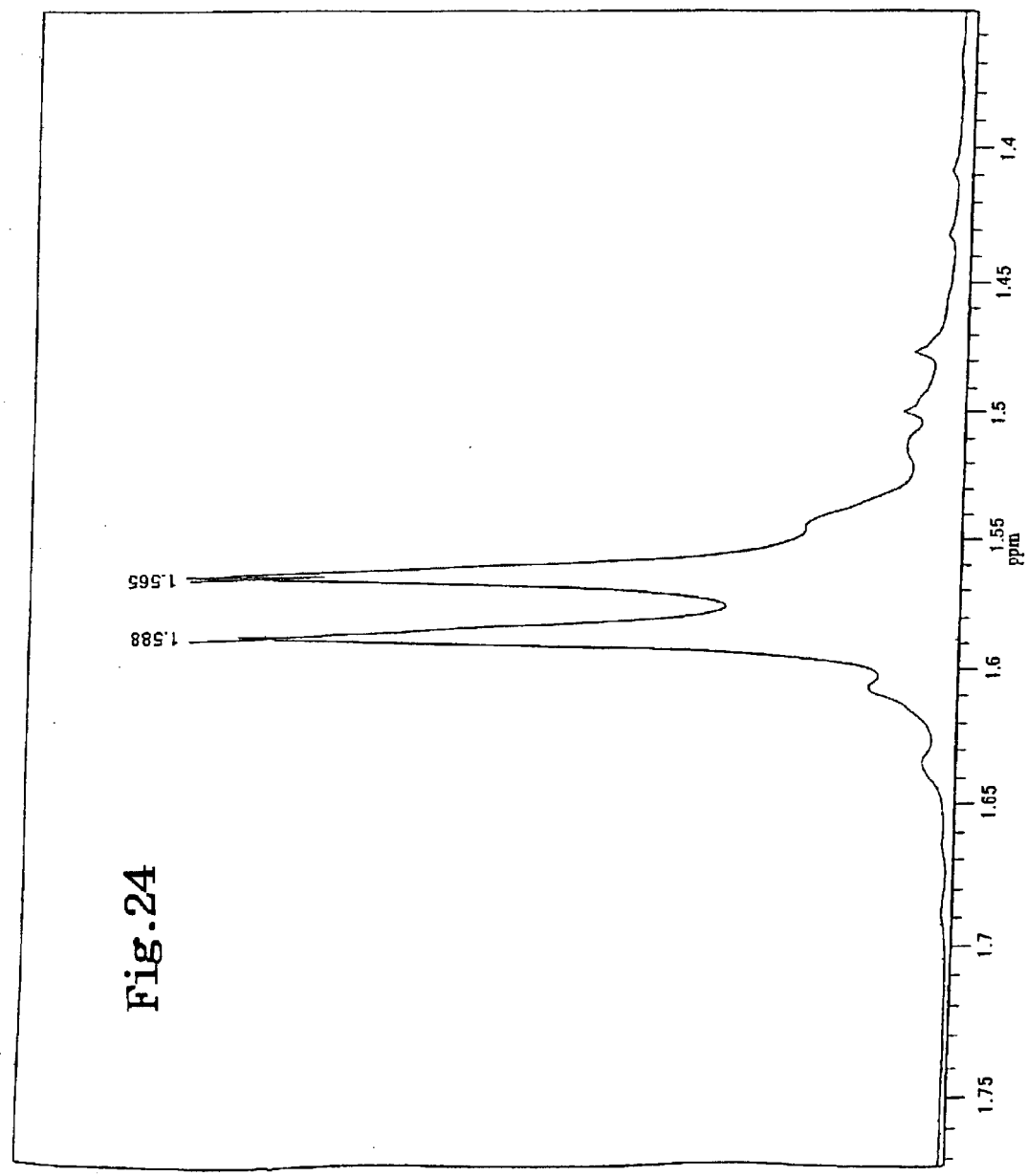
FIG. 24 shows a partial scale view of NMR of FIG. 23.
Figure 25:
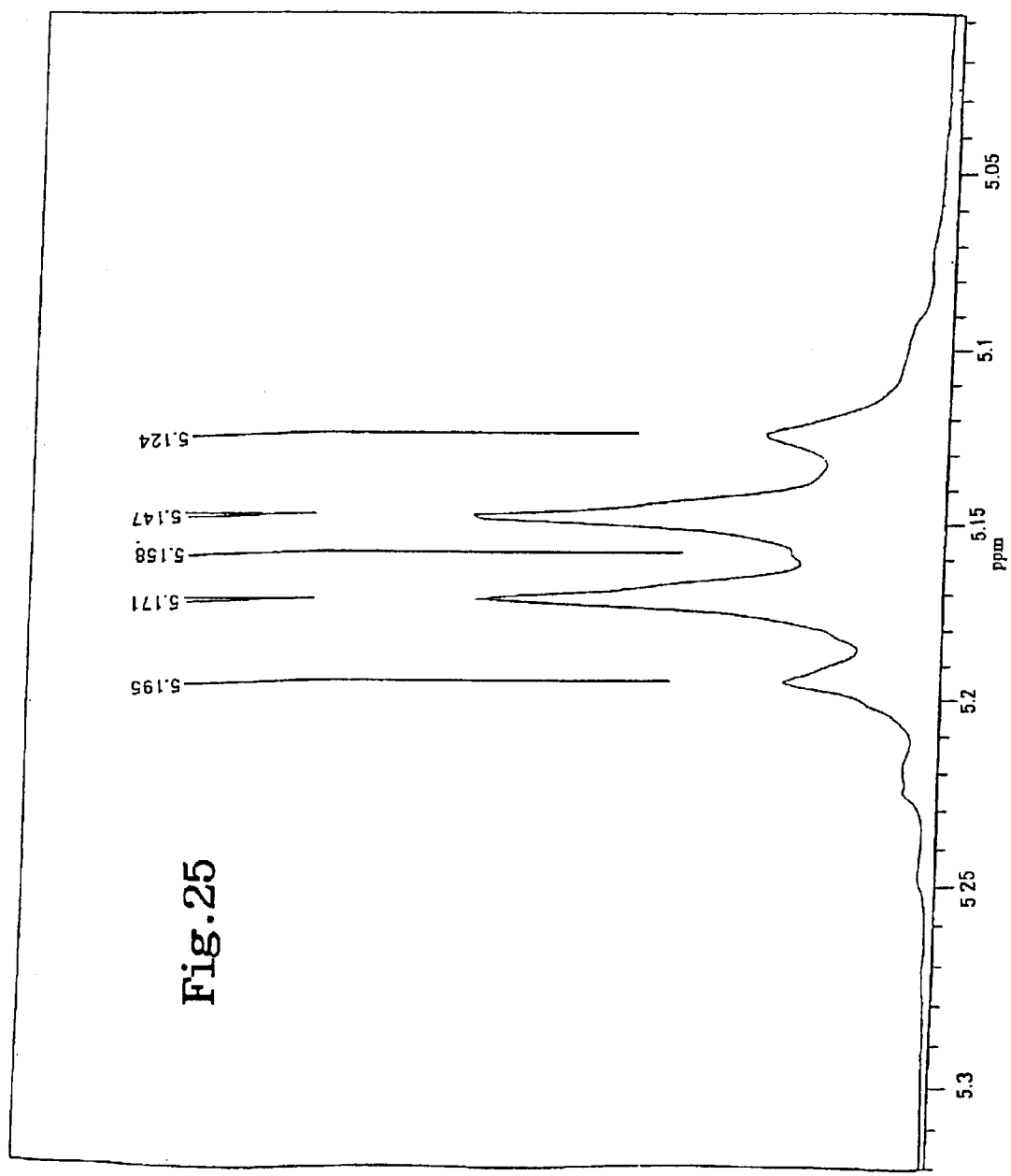
FIG. 25 shows a partial scale view of NMR of FIG. 23.

A general view of NMR of the product obtained in Example 8 is shown in FIG. 23, and scale views of a part of FIG. 23 are shown in FIGS. 24 and 25.

Example 9

A THF solution (2 ml) in which 0.132 g (1.00 mmol) of t-butyldimethylsilanol was dissolved was added to a 25 ml double-cap eggplant-shaped flask under a nitrogen atmosphere, and cooled to 0° C. Then, 0.64 ml (1.00 mmol) of n-butyllithium was added thereto and the mixture was stirred for 15 minutes. Further, a THF solution (2 ml) in which 0.434 g (3.01 mmol) of (3R,6R)-(+)-3,6-dimethyl-1,4-dioxane-2,5-dione was dissolved was added thereto and stirred, and the temperature was gradually raised to room temperature over 2.5 hours.

After completion of stirring, 2 ml of saturated ammonium chloride was added to the mixture while maintaining a nitrogen atmosphere, and 10 ml of water was further added thereto. The mixture was extracted with chloroform and a saturated saline solution and washed, and then anhydrous sodium sulfate was added thereto and dried overnight. The obtained product was subjected to vacuum concentration in which solvent was completely removed with a vacuum pump. As a result, 0.537 g (yield 82.5%) of cyclic oligo-lactate wherein all asymmetric carbon atoms have an R configuration, was obtained.

Figure 26:
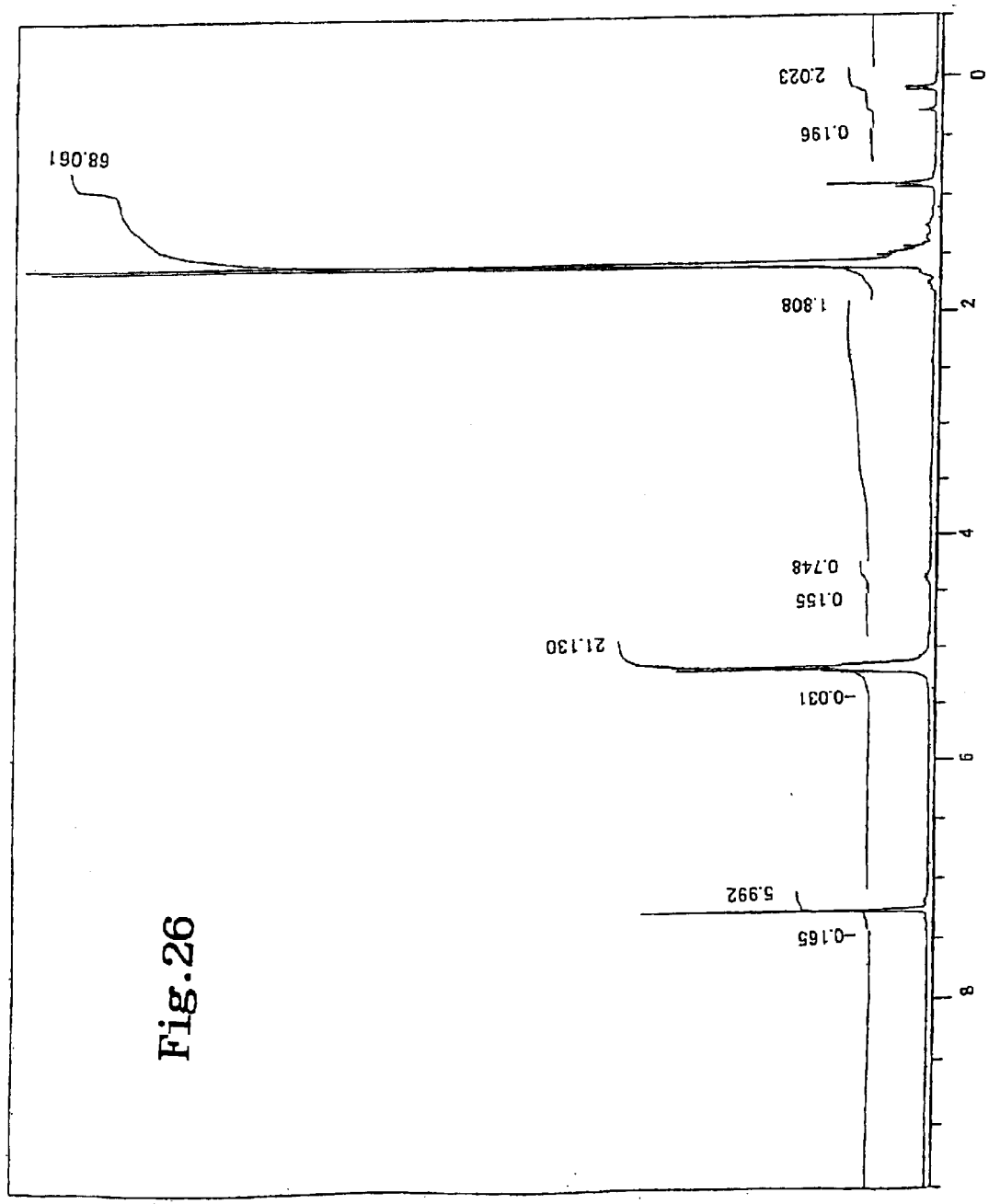
FIG. 26 shows a general view of NMR of the product obtained in Example 9.
Figure 27:
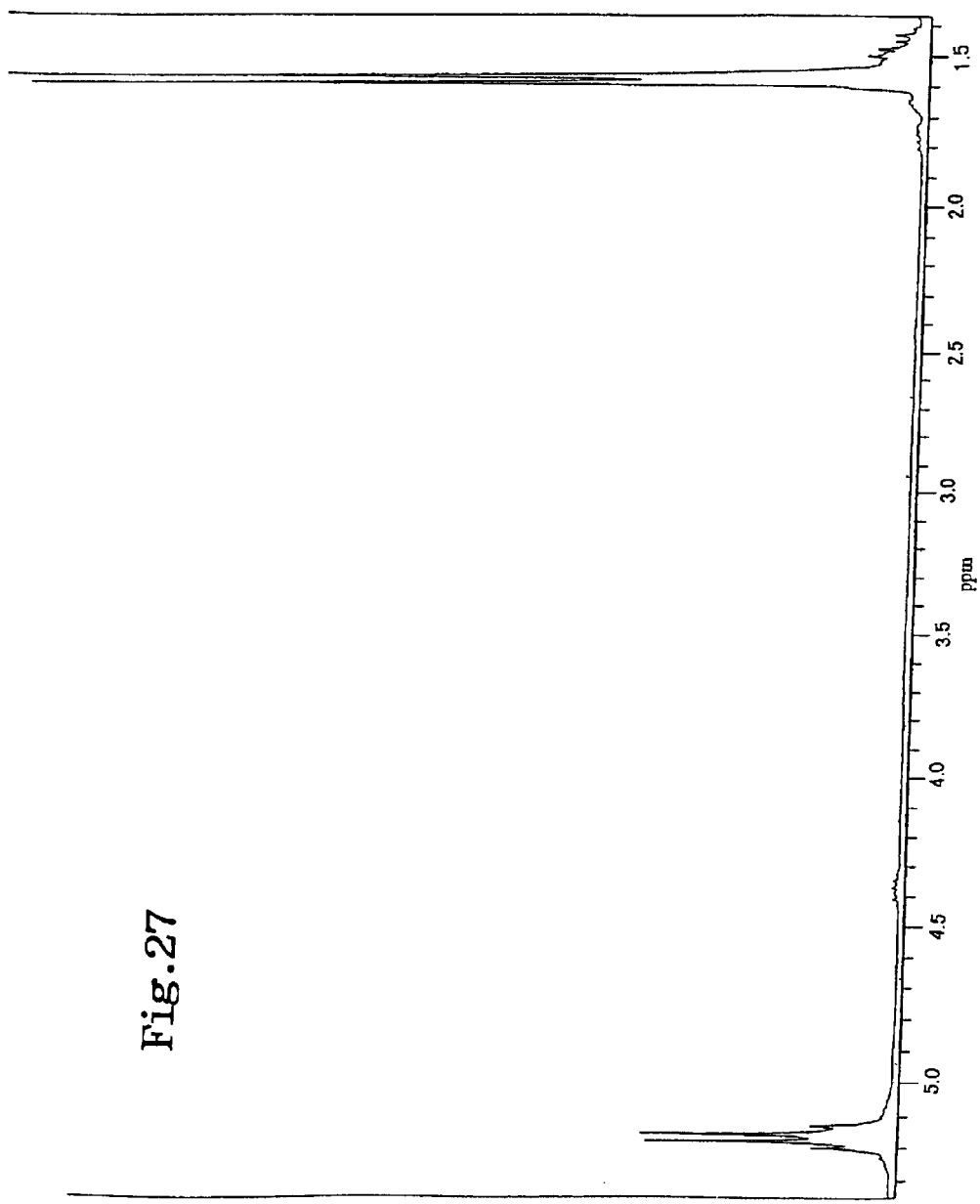
FIG. 27 shows a partial scale view of NMR of FIG. 26.

A general view of NMR of the product obtained by Example 9 is shown in FIG. 26, and a scale view of a part of FIG. 26 is shown in FIG. 27.

Example 10

3 ml of THF solution containing 0.118 g (1 mmol) of ethyl S-lactate was added to a 50 ml double-cap eggplant-shaped flask at room temperature under a nitrogen atmosphere, and 0.64 ml (1.00 mmol) of n-butyllithium was reacted therewith at −78° C. followed by stirring for 15 minutes. Further, 2 ml of THF solution containing 0.576 g (4 mmol) of L-(−)-lactide was added thereto and reacted therewith for 30 minutes, and then the temperature was raised from −78° C. to 0° C. followed by reaction for 1.5 hours. Subsequently, the temperature was further raised to room temperature by addition of 5 ml of saturated ammonium chloride solution. After the mixture was extracted with chloroform, the organic layer was washed with a saturated saline solution, and dried with anhydrous sodium sulfate followed by vacuum concentration (NMR sa0140), to obtain the residue.

Figure 28:
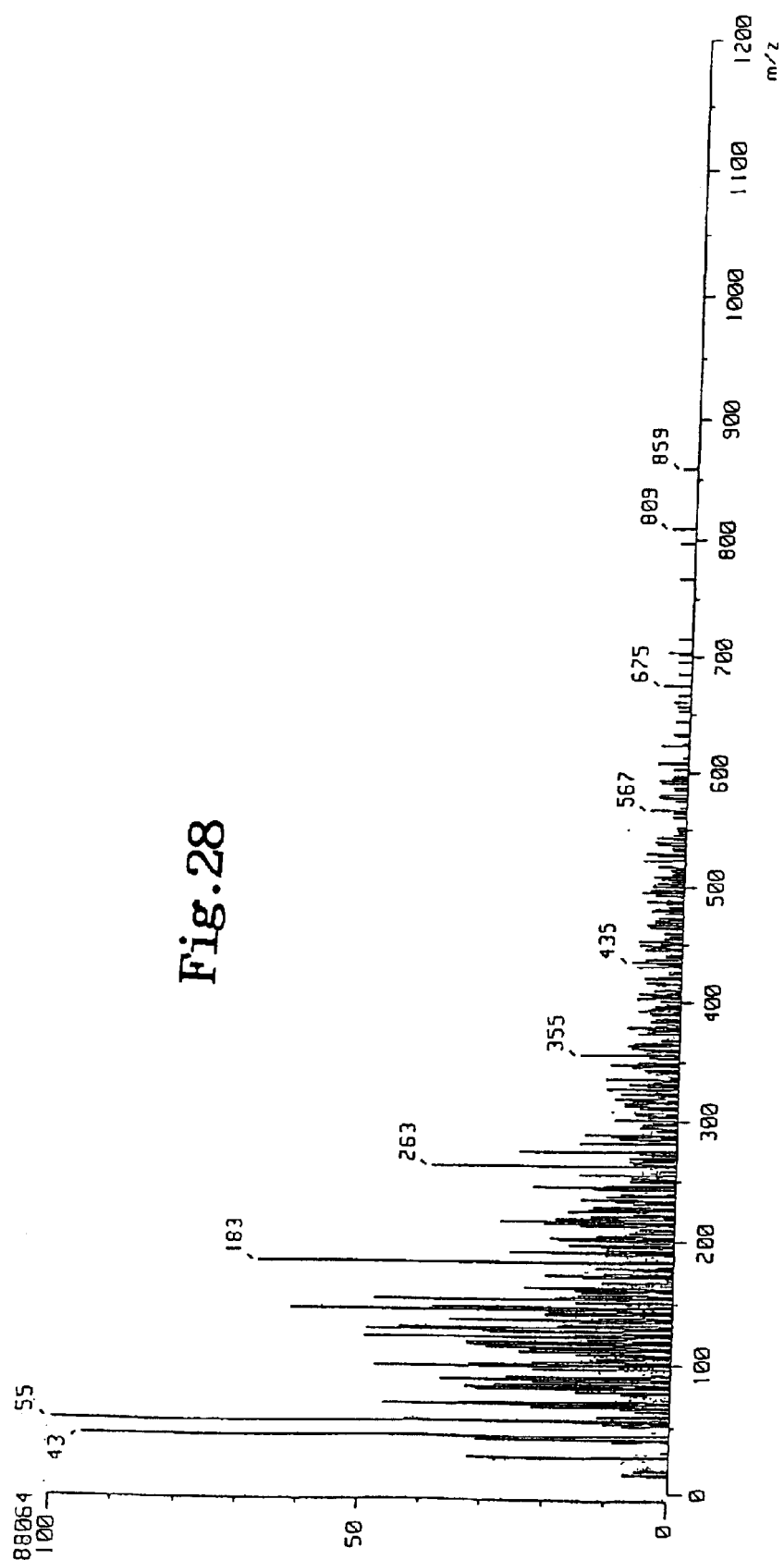
FIG. 28 shows an MS spectrum of the product obtained in Example 10.
Figure 29:
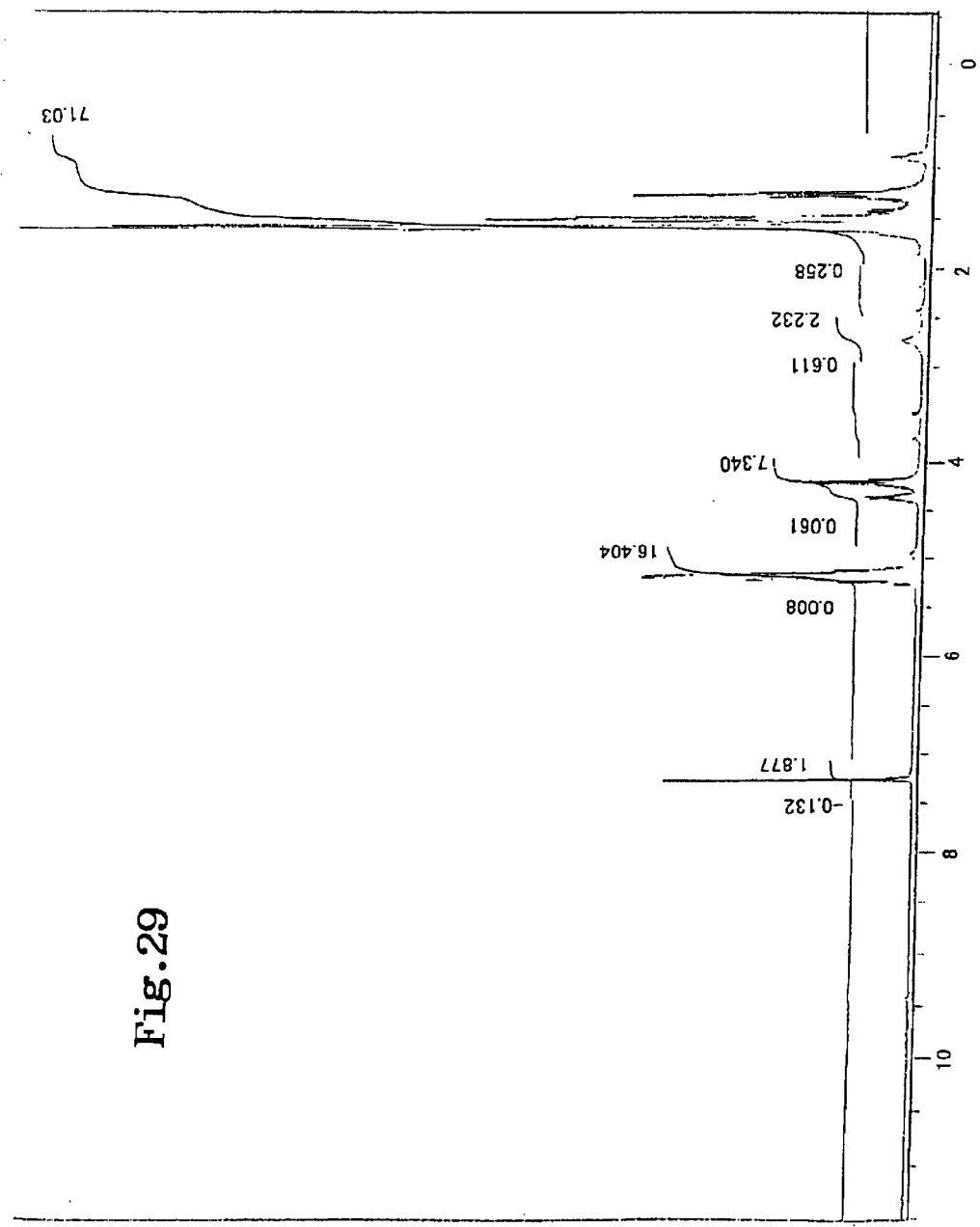
FIG. 29 shows a general view of NMR of the product obtained in Example 10.
Figure 30:
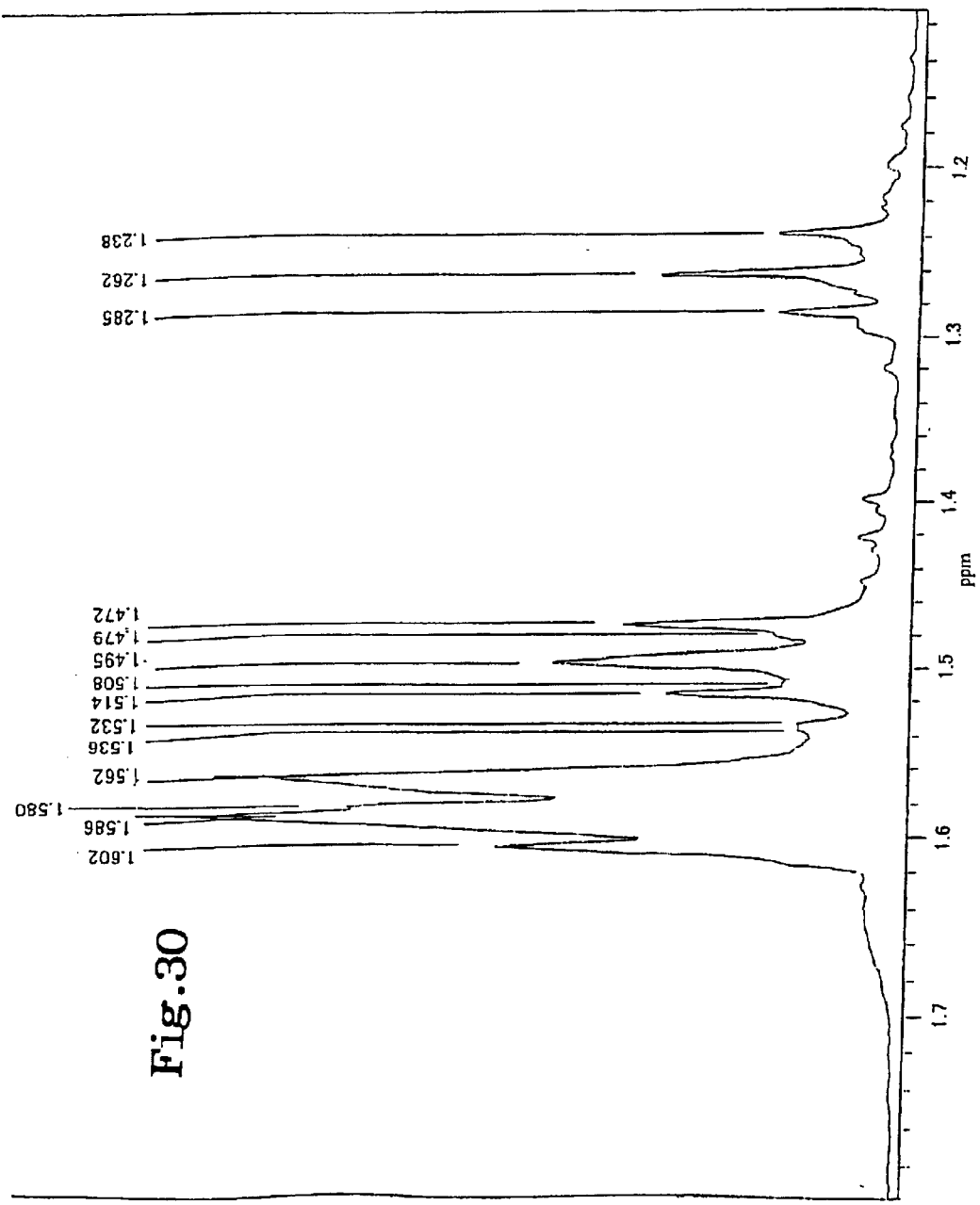
FIG. 30 shows a partial scale view of NMR of FIG. 29.
Figure 31:
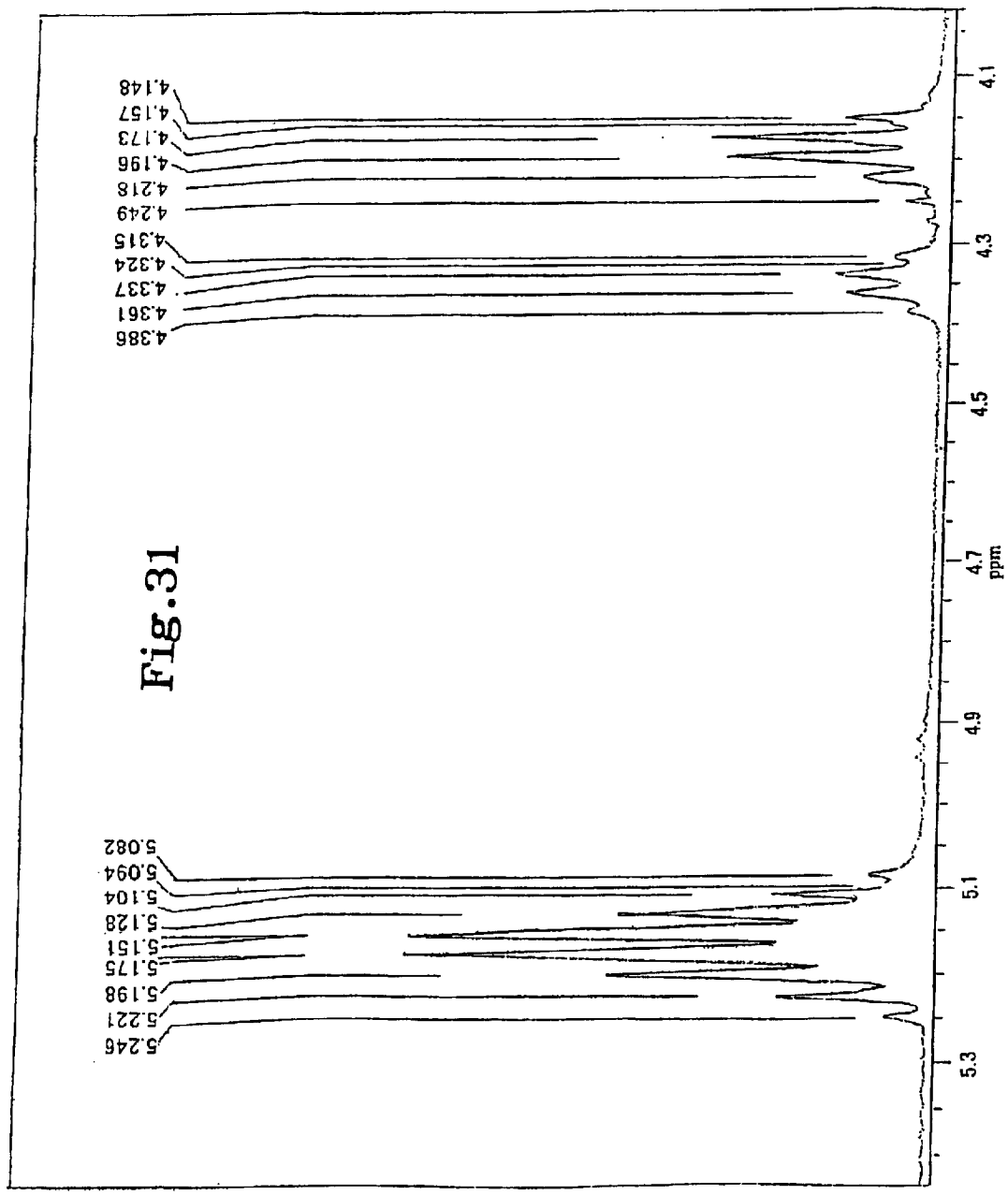
FIG. 31 shows a partial scale view of NMR of FIG. 29.

An MS spectrum of the product obtained in Example 10 is shown in FIG. 28. In addition, a general view of NMR of the product obtained in Example 10 is shown in FIG. 29, and scale views of a part of FIG. 29 are shown in FIGS. 30 and 31.

INDUSTRIAL APPLICABILITY

According to the method for producing a cyclic lactic acid oligomer of the present invention, a cyclic lactic acid oligomer can be produced at good yield, and its industrial significance is great. In addition, a cyclic lactic acid oligomer produced by the production method of the present invention is useful as a tumor cell growth inhibiting agent, antineoplastic agent, preventive agent against cancer metastasis, QOL improving agent for cancer patients, immune activating agent, therapeutic agent for diabetes, antiobestic agent, an agent for promoting glycogen accumulation or an agent for enhancing physical fitness. Furthermore, the cyclic lactic acid oligomer is useful not only as a medicament, but also as various types of health foods and diet supplements including soft drinks, drinkable preparations, health foods, specific hygienic foods, functional foods, function activating food, nutritional supplementary foods, supplements, feed, feed additives, and the like.

What is claimed is:

1. A method for producing a cyclic lactic acid oligomer represented by the following formula (1):

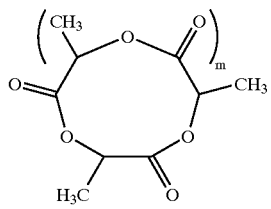

(1)

wherein m represents an integer of 1 to 30, wherein lactides are polymerized in the presence of an alkali metal compound represented by the following formula (2):

(2)

wherein R represents an aliphatic group, aromatic group, —Si($R^{10}$)($R^{11}$)($R^{12}$), —CH($R^{20}$)CONR$^{21}$R$^{22}$ or —CH($R^{30}$)COOR$^{31}$, wherein each of $R^{10}$, $R^{11}$ and $R^{12}$ independently represents an aliphatic or aromatic group, $R^{20}$ represents an aliphatic group, each of $R^{21}$ and $R^{22}$ independently represents a hydrogen atom, aliphatic group or aromatic group, $R^{30}$ represents an aliphatic group, and $R^{31}$ represents a hydrogen atom, aliphatic group or aromatic group;

Y represents —O—, —S— or —NR$^{40}$—, wherein R$^{40}$ represents a hydrogen atom, aliphatic group or aromatic group; and Me represents an alkali metal.

2. The method for producing a cyclic lactic acid oligomer according to claim 1, wherein said alkali metal compound is a compound of formula (2) wherein R represents an alkyl group having 1 to 12 carbon atoms, aryl group having 6 to 30 carbon atoms, —Si($R^{10}$)($R^{11}$)($R^{12}$), —CH($R^{20}$)CONR$^{21}$R$^{22}$ or —CH($R^{30}$)COOR$^{31}$, wherein each of $R^{10}$, $R^{11}$ and $R^{12}$ independently represents an aliphatic or aromatic group, $R^{20}$ represents an aliphatic group, each of $R^{21}$ and $R^{22}$ independently represents a hydrogen atom, aliphatic group or aromatic group, $R^{30}$ represents an aliphatic group, and $R^{31}$ represents a hydrogen atom, aliphatic group or aromatic group.

3. The method for producing a cyclic lactic acid oligomer according to claim 1, wherein said alkali metal compound is a compound of formula (2) wherein Y is —O— or —S—.

4. The method for producing a cyclic lactic acid oligomer according to claim 1, wherein said alkali metal compound is a compound of formula (2) wherein Me is lithium.

5. The method for producing a cyclic lactic acid oligomer according to claim 1, wherein, in formula (1), m is an integer of 1 to 21.

6. The method for producing a cyclic lactic acid oligomer according to claim 1, wherein said alkali metal compound is any of:

a compound of formula (2) wherein R is an aliphatic group having 4 or more carbon atoms; a compound of formula (2) wherein R is an aromatic group and Y is —S—; or a compound of formula (2) wherein R is —CH($R^{20}$)CONR$^{21}$R$^{22}$ wherein $R^{20}$ represents an aliphatic group and each of $R^{21}$ and $R^{22}$ independently represents a hydrogen atom, aliphatic group or aromatic group.

7. The method for producing a cyclic lactic acid oligomer according to claim 6, wherein cyclic lactic acid oligomer is selectively produced substantially free of chain lactic acid oligomer.

8. The method for producing a cyclic lactic acid oligomer according to claim 2, wherein said alkali metal compound is a compound of formula (2) wherein Y is —O— or —S—.

9. The method for producing a cyclic lactic acid oligomer according to claim 2, wherein said alkali metal compound is a compound of formula (2) wherein Me is lithium.

10. The method for producing a cyclic lactic acid oligomer according to claim 3, wherein said alkali metal compound is a compound of formula (2) wherein Me is lithium.

11. The method for producing a cyclic lactic acid oligomer according to claim 2, wherein, in formula (1), m is an integer of 1 to 21.

12. The method for producing a cyclic lactic acid oligomer according to claim 3, wherein, in formula (1), m is an integer of 1 to 21.

13. The method for producing a cyclic lactic acid oligomer according to claim 4, wherein, in formula (1), m is an integer of 1 to 21.

14. The method for producing a cyclic lactic acid oligomer according to claim 2, wherein said alkali metal compound is any of:

a compound of formula (2) wherein R is an aliphatic group having 4 or more carbon atoms; a compound of formula (2) wherein R is an aromatic group and Y is —S—; or a compound of formula (2) wherein R is —CH($R^{20}$)CONR$^{21}$R$^{22}$ wherein $R^{20}$ represents an aliphatic group and each of $R^{21}$ and $R^{22}$ independently represents a hydrogen atom, aliphatic group or aromatic group.

15. The method for producing a cyclic lactic acid oligomer according to claim 3, wherein said alkali metal compound is any of:

a compound of formula (2) wherein R is an aliphatic group having 4 or more carbon atoms; a compound of formula (2) wherein R is an aromatic group and Y is —S—; or a compound of formula (2) wherein R is —CH($R^{20}$)CONR$^{21}$R$^{22}$ wherein $R^{20}$ represents an aliphatic group and each of $R^{21}$ and $R^{22}$ independently represents a hydrogen atom, aliphatic group or aromatic group.

16. The method for producing a cyclic lactic acid oligomer according to claim 4, wherein said alkali metal compound is any of:

a compound of formula (2) wherein R is an aliphatic group having 4 or more carbon atoms; a compound of formula (2) wherein R is an aromatic group and Y is —S—; or a compound of formula (2) wherein R is —CH($R^{20}$)CONR$^{21}$R$^{22}$ wherein $R^{20}$ represents an aliphatic group and each of $R^{21}$ and $R^{22}$ independently represents a hydrogen atom, aliphatic group or aromatic group.

17. The method for producing a cyclic lactic acid oligomer according to claim 5, wherein said alkali metal compound is any of:

a compound of formula (2) wherein R is an aliphatic group having 4 or more carbon atoms; a compound of formula (2) wherein R is an aromatic group and Y is —S—; or a compound of formula (2) wherein R is —CH($R^{20}$)CONR$^{21}$R$^{22}$ wherein $R^{20}$ represents an aliphatic group and each of $R^{21}$ and $R^{22}$ independently represents a hydrogen atom, aliphatic group or aromatic group.

18. The method for producing a cyclic lactic acid oligomer according to claim 14, wherein cyclic lactic acid oligomer is selectively produced substantially free of chain lactic acid oligomer.

19. The method for producing a cyclic lactic acid oligomer according to claim 15, wherein cyclic lactic acid oligomer is selectively produced substantially free of chain lactic acid oligomer.

20. The method for producing a cyclic lactic acid oligomer according to claim 16, wherein cyclic lactic acid oligomer is selectively produced substantially free of chain lactic acid oligomer.

* * * * *

UNITED STATES PATENT AND TRADEMARK OFFICE
CERTIFICATE OF CORRECTION

PATENT NO. : 6,825,314 B1
DATED : November 30, 2004
INVENTOR(S) : M. Watanabe et al.

It is certified that error appears in the above-identified patent and that said Letters Patent is hereby corrected as shown below:

<u>Title page,</u>
Item [56], References Cited, OTHER PUBLICATIONS,
"English Lanuage Abstract" reference, "6-309264" should be -- 6-306264 --.

Signed and Sealed this

Twelfth Day of July, 2005

JON W. DUDAS
*Director of the United States Patent and Trademark Office*